(12) United States Patent
Xie et al.

(10) Patent No.: US 11,951,227 B2
(45) Date of Patent: *Apr. 9, 2024

(54) NANOFIBER STRUCTURES AND METHODS OF USE THEREOF

(71) Applicant: BOARD OF REGENTS OF THE UNIVERSITY OF NEBRASKA, Lincoln, NE (US)

(72) Inventors: Jingwei Xie, Omaha, NE (US); Shixuan Chen, Omaha, NE (US); Mark Carlson, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/712,601

(22) Filed: Apr. 4, 2022

(65) Prior Publication Data
US 2022/0226537 A1 Jul. 21, 2022

Related U.S. Application Data

(63) Continuation of application No. 16/336,276, filed as application No. PCT/US2017/053921 on Sep. 28, 2017, now Pat. No. 11,318,224.

(60) Provisional application No. 62/400,700, filed on Sep. 28, 2016.

(51) Int. Cl.
| | |
|---|---|
| *A61L 24/04* | (2006.01) |
| *A61K 9/70* | (2006.01) |
| *A61L 24/00* | (2006.01) |
| *A61L 24/10* | (2006.01) |
| *A61L 27/18* | (2006.01) |
| *A61L 27/22* | (2006.01) |
| *A61L 27/34* | (2006.01) |
| *A61L 27/52* | (2006.01) |
| *A61L 27/54* | (2006.01) |
| *D01D 5/00* | (2006.01) |
| *D06M 11/01* | (2006.01) |
| *D06M 101/32* | (2006.01) |
| *D06N 3/00* | (2006.01) |

(52) U.S. Cl.
CPC .......... *A61L 24/046* (2013.01); *A61K 9/7007* (2013.01); *A61L 24/0015* (2013.01); *A61L 24/0031* (2013.01); *A61L 24/104* (2013.01); *A61L 27/18* (2013.01); *A61L 27/222* (2013.01); *A61L 27/34* (2013.01); *A61L 27/52* (2013.01); *A61L 27/54* (2013.01); *D01D 5/0007* (2013.01); *D06M 11/01* (2013.01); *A61L 2300/404* (2013.01); *A61L 2300/414* (2013.01); *A61L 2300/418* (2013.01); *A61L 2400/04* (2013.01); *A61L 2400/12* (2013.01); *D06M 2101/32* (2013.01); *D06N 3/0004* (2013.01); *D06N 2203/026* (2013.01); *D06N 2203/028* (2013.01); *D06N 2203/041* (2013.01); *D10B 2509/022* (2013.01)

(58) Field of Classification Search
CPC .............. A61L 24/046; A61L 24/0031; A61L 24/0015; A61L 24/104; A61L 27/18; A61L 27/222; A61L 27/34; A61L 27/52; A61L 27/54; A61L 2400/04; A61L 2400/12; A61L 2300/404; A61L 2300/414; A61L 2300/418; D06M 11/01; D06M 2101/32; A61K 9/7007; D06N 2203/026; D06N 3/0041; D06N 2203/028; D06N 2203/041; D10B 2509/022

See application file for complete search history.

(56) References Cited

U.S. PATENT DOCUMENTS

| | | |
|---|---|---|
| 3,674,540 A | 7/1972 | Pergaminos |
| 6,653,005 B1 | 11/2003 | Muradov |
| 7,704,740 B2 | 4/2010 | Schindler et al. |
| 9,403,958 B2 | 8/2016 | Lindner et al. |
| 9,655,995 B2 | 5/2017 | Xie |
| 9,913,862 B2 | 3/2018 | Collins et al. |
| 10,799,620 B2 | 10/2020 | Xie et al. |
| 11,033,659 B2 | 6/2021 | Xie et al. |
| 11,318,224 B2 | 5/2022 | Xie et al. |
| 11,427,936 B2 | 8/2022 | Xie |
| 2005/0084532 A1 | 4/2005 | Howdle et al. |
| 2005/0187330 A1 | 8/2005 | Gulari et al. |
| 2006/0002978 A1 | 1/2006 | Shea et al. |
| 2007/0077272 A1 | 4/2007 | Li et al. |
| 2008/0112998 A1 | 5/2008 | Wang |
| 2010/0183699 A1 | 7/2010 | Wan et al. |
| 2011/0070151 A1 | 3/2011 | Braithwaite et al. |
| 2011/0195123 A1 | 8/2011 | Shemi |
| 2011/0293685 A1 | 12/2011 | Kuo et al. |
| 2012/0040581 A1 | 2/2012 | Kim |

(Continued)

FOREIGN PATENT DOCUMENTS

| | | |
|---|---|---|
| CN | 102068716 A | 5/2011 |
| CN | 102071485 A | 5/2011 |

(Continued)

OTHER PUBLICATIONS

Liu et al. Electrospun nanofibers for regenerative medicine Adv. Healthc.Mater.(2012)1(1):10-25.*

(Continued)

*Primary Examiner* — Shirley V Gembeh
(74) *Attorney, Agent, or Firm* — Robert C. Netter, Jr.; Dann, Dorfman, Herrell & Skillman

(57) ABSTRACT

Coated and expanded, nanofiber structures are provided and methods of use thereof.

38 Claims, 12 Drawing Sheets

(56) References Cited

U.S. PATENT DOCUMENTS

| | | |
|---|---|---|
| 2012/0226295 A1 | 9/2012 | Jabbari |
| 2013/0095167 A1 | 4/2013 | Warnke |
| 2013/0112625 A1 | 5/2013 | Bahukudumbi et al. |
| 2014/0024760 A1 | 1/2014 | Kwon et al. |
| 2014/0051169 A1 | 2/2014 | Ganey et al. |
| 2016/0015792 A1 | 1/2016 | Hendricus van Pinxteren et al. |
| 2016/0015952 A1 | 1/2016 | Omachi et al. |
| 2016/0106548 A1 | 4/2016 | Li et al. |
| 2016/0176714 A1 | 6/2016 | Do et al. |
| 2017/0296703 A1 | 10/2017 | Xie et al. |
| 2020/0164107 A1 | 5/2020 | Xie et al. |
| 2020/0277711 A1 | 9/2020 | Xie |
| 2021/0268154 A1 | 9/2021 | Xie et al. |

FOREIGN PATENT DOCUMENTS

| | | |
|---|---|---|
| CN | 102703996 A | 10/2012 |
| CN | 103382625 A | 11/2013 |
| CN | 104464712 A | 3/2015 |
| CN | 106421898 A | 2/2017 |
| CN | 106492289 A | 3/2017 |
| CN | 106563172 A | 4/2017 |
| CN | 106620881 A | 5/2017 |
| CN | 105012991 B | 1/2018 |
| EP | 1611877 A1 | 1/2006 |
| EP | 2813212 A1 | 12/2014 |
| JP | 2006-169497 A | 6/2006 |
| JP | 2007160691 A | 6/2007 |
| JP | 2007222477 A | 9/2007 |
| JP | 4656320 B2 | 3/2011 |
| KR | 101493444 B1 | 2/2015 |
| WO | 00/50104 A1 | 8/2000 |
| WO | 2006/019600 A2 | 2/2006 |
| WO | 2018/227078 A1 | 12/2008 |
| WO | 2009/011658 A1 | 1/2009 |
| WO | 2009/088777 A1 | 7/2009 |
| WO | 2014/037651 A1 | 3/2014 |
| WO | 2014/191739 A1 | 12/2014 |
| WO | 2015/051042 A2 | 4/2015 |
| WO | 2016/053988 A1 | 4/2016 |
| WO | 2018/017929 A1 | 1/2018 |
| WO | 2019/060393 A1 | 3/2019 |

OTHER PUBLICATIONS

Wei, et al., "The multifunctional wound dressing with core-shell structured fibers prepared by coaxial electrospinning" Front. Mater. Sci. (2016) 10(2):113-121.

Kang, et al., "Chitosan-coated poly(vinyl alcohol) nanofibers for wound dressings" J. Biomed. Mater. Res. B Appl. Biomater. (2010) 92(2):568-76.

Fu, L., et al., "Three-dimensional nanofiber scaffolds with arrayed holes for engineering skin tissue constructs" MRS Communications (2017) 7:361-366.

Liu, Y., et al., "Composite vascular scaffold combining electrospun fibers and physically-crosslinked hydrogel with copper wire-induced grooves structure" J. Mech. Behav. Biomed. Mater. (2016) 61:12-25.

Nazarov, R., et al., "Porous 3-D scaffolds from regenerated silk fibroin" Biomacromolecules (2004) 5(3):718-26.

Bencherif, S.A., et al., "Advances in the design of macroporous polymer scaffolds for potential applications in dentistry" J. Periodontal Implant Sci. (2013) 43(6):251-61.

Xie, J., et al., "Putting Electrospun Nanofibers to Work for Biomedical Research" Macromol. Rapid Commun. (2008) 29:1775-1792.

Jiang, J., et al., "Expanding Two-Dimensional Electrospun Nanofiber Membranes in the Third Dimension By a Modified Gas-Foaming Technique" ACS Biomater. Sci. Eng. (2015) 1(10):991-1001.

Liu, W., et al., "Electrospun nanofibers for regenerative medicine" Adv. Healthc. Mater. (2012) 1(1):10-25.

Nam, Y.S., et al., "A Novel Fabrication Method of Macroporous Biodegradable Polymer Scaffolds Using Gas Foaming Salt as a Porogen Additive" J. Biomed. Mater. Res. (2000) 53(1):1-7.

Lee, Y.H., et al., "Electrospun dual-porosity structure and biodegradation morphology of Montmorillonite reinforced PLLA nanocomposite scaffolds" Biomaterials (2005) 26:3165-3172.

Jiang, J., et al., "Local Sustained Delivery of 25-Hydroxyvitamin D3 for Production of Antimicrobial Peptides" Pharm. Res. (2015) 32(9): 2851-2862.

Ma, B., et al., "Rational design of nanofiber scaffolds for orthopedic tissue repair and regeneration" Nanomedicine (2013) 8(9):1459-81.

Chen, S., et al.,. "Recent advances in electrospun nanofibers for wound healing" Nanomedicine (Lond.) (2017) 12 (11):1335-1352.

Xie, J., et al., "The differentiation of embryonic stem cells seeded on electrospun nanofibers into neural lineages" Biomaterials (2009) 30(3):354-362.

Xie, J, et al., "Controlled biomineralization of electrospun poly(ε-caprolactone) fibers for enhancing their mechanical properties" Acta Biomaterialia (2013) 9(3):5698-5707.

Dehghani, et al., "Engineering porous scaffolds using gas-based techniques" Current Opinion in Biotechnology (2011) 22:661-666.

Mulmi, et al., "Fabrication of Air Freshening Spongy Three Dimensional Electrospun Membrane" Journal of the Institute of Engineering (2018) 14(1):14-21.

Keit, et al., "Expansion of Two-dimension Electrospun Nanofiber Mats into Three-dimension Scaffolds" J. Vis. Exp. (2018):e58918.

Jiang, J., et al., "Expanded Three-dimensional Nanofiber Scaffolds: Cell Penetration, Neovascularization, and Host Response" Adv. Healthc. Mater. (2016) 5(23): 2993-3003.

Jiang, J., et al., "CO2-Expanded Nanofiber Scaffolds Maintain Activity of Encapsulated Bioactive Materials and Promote Cellular Infiltration and Positive Host Response" Acta Biomater. (2018) 68: 237-248.

Hwang, P.T.J., et al., "Poly(ε-caprolactone)/gelatin composite electrospun scaffolds with porous crater-like structures for tissue engineering" J Biomed Mater Res A. (2016) 104(4):1017-1029.

Liu, Y., et al., "HB-EGF embedded in PGA/PLLA scaffolds via subcritical CO2 augments the production of tissue engineered intestine" Biomaterials (2016) 103:150-159.

Borjigin, M., et al., "Proliferation of Genetically Modified Human Cells on Electrospun Nanofiber Scaffolds" Mol. Ther.-Nuc. Acids (2012) 1:e59.

Geiger, B.C., et al., "Dual drug release from CO2-infused nanofibers via hydrophobic and hydrophilic interactions" J. Appl. Polym. Sci. (2015) 132:42571.

Ayodeji, O., et al., "Carbon dioxide impregnation of electrospun polycaprolactone fibers" J. Supercritical Fluids (2007) 41:173-178.

Lee, S.J., et al., "The use of thermal treatments to enhance the mechanical properties of electrospun poly(E-caprolactone) scaffolds" Biomaterials (2008) 29:1422-1430.

Xie, J., et al., "Electrospray in the dripping mode for cell microencapsulation" J. Colloid Interface Sci. (2007) 312:247-255.

Cai, H., et al., "Aerogel Microspheres from Natural Cellulose Nanofibrils and Their Application as Cell Culture Scaffold" Biomacromolecules (2014) 15:2540-2547.

Wang, W., et al., "Dentin regeneration by stem cells of apical papilla on injectable nanofibrous microspheres and stimulated by controlled BMP-2 release" Acta Biomater. (2016) 36:63-72.

Gu, B.K., et al., "Fabrication of sonicated chitosan nanofiber mat with enlarged porosity for use as hemostatic materials" Carbohydr. Polym. (2013) 97(1):65-73.

Electrospin Tech, "Post-electrospinning expansion of 2D membrane to 3D scaffold using gas foaming" (Oct. 27, 2015) available at: http://electrospintech.com/gasfoam3d.html#.X5bnPC9h0kg.

Pok, S., et al., "A multilayered scaffold of a chitosan and gelatin hydrogel supported by a PCL core for cardiac tissue engineering" Acta Biomater. (2013) 9(3):5630-5642.

Zhao, Y., et al., "Preparation of Nanofibers with Renewable Polymers and Their Application in Wound Dressing" Intl. J. Polmer Sci. (2016) 2016:4672839.

(56) References Cited

OTHER PUBLICATIONS

Joshi, M.K., et al., "Multi-layered macroporous three-dimensional nanofibrous scaffold via a novel gas foaming technique" Chem. Engr. J. (2015) 275:79-88.

* cited by examiner

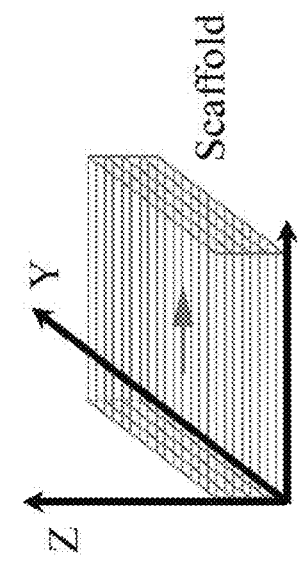
Figure 1A
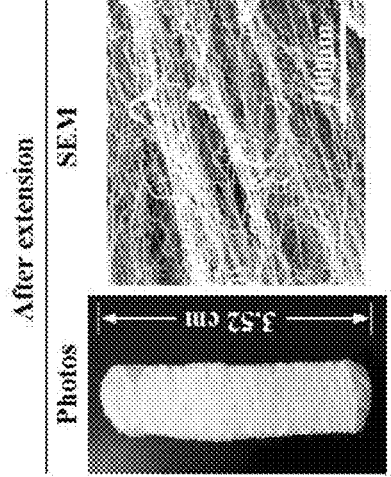
Figure 1B
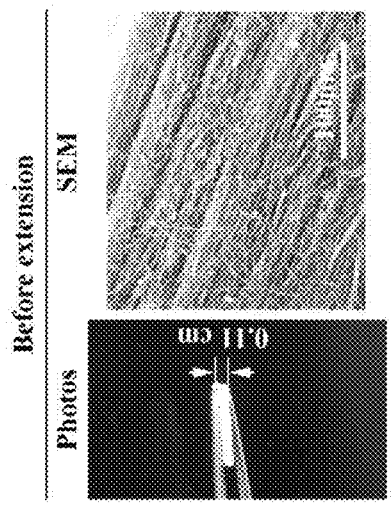
Figure 1C
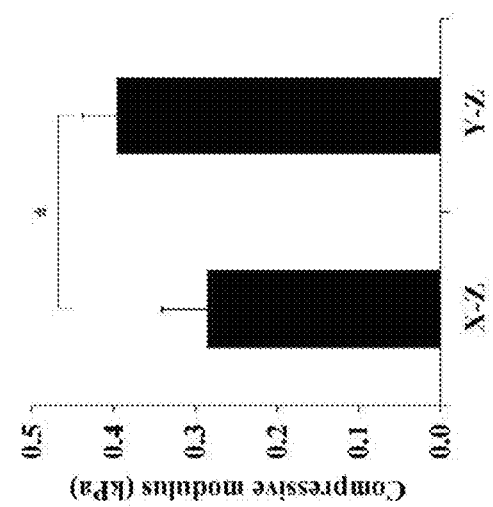
Figure 1D
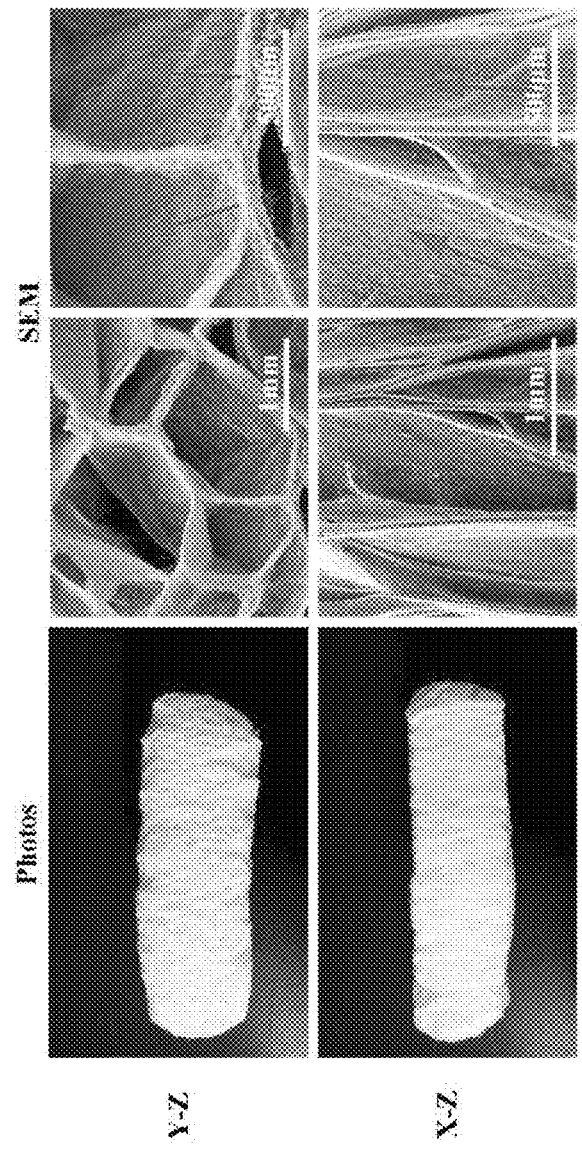

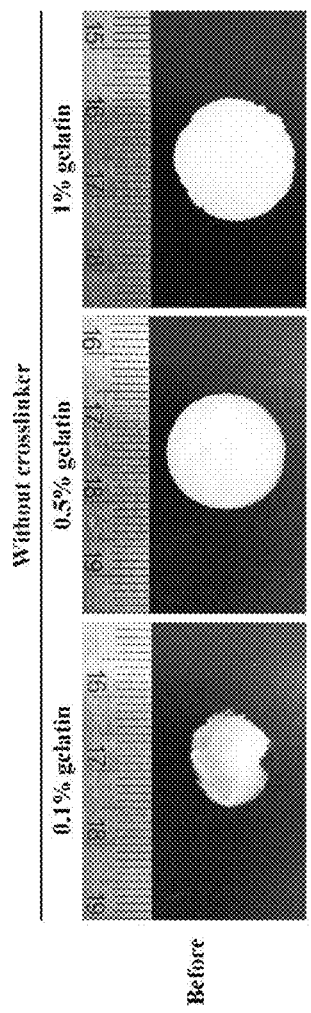
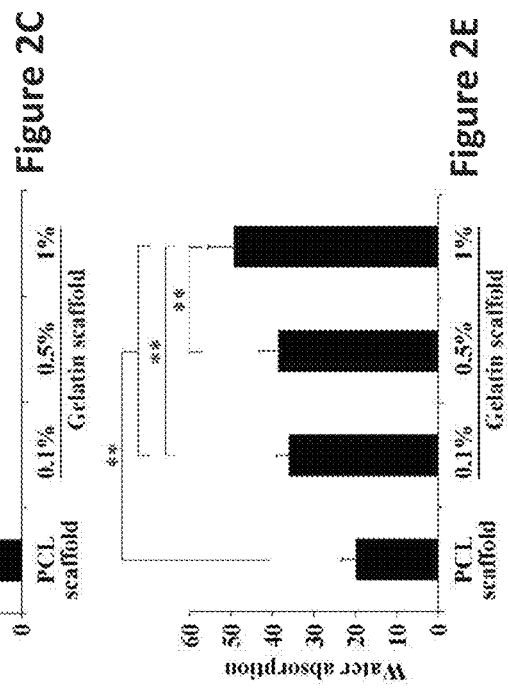
Figure 2A
Figure 2B
Figure 2C
Figure 2D
Figure 2E

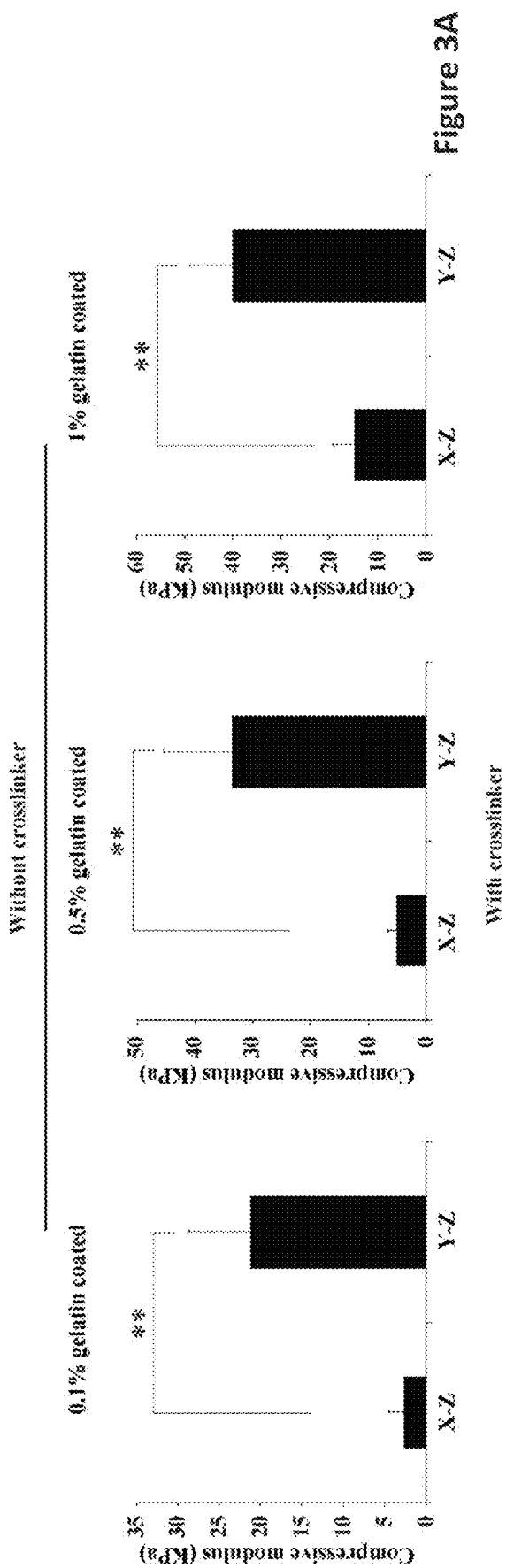
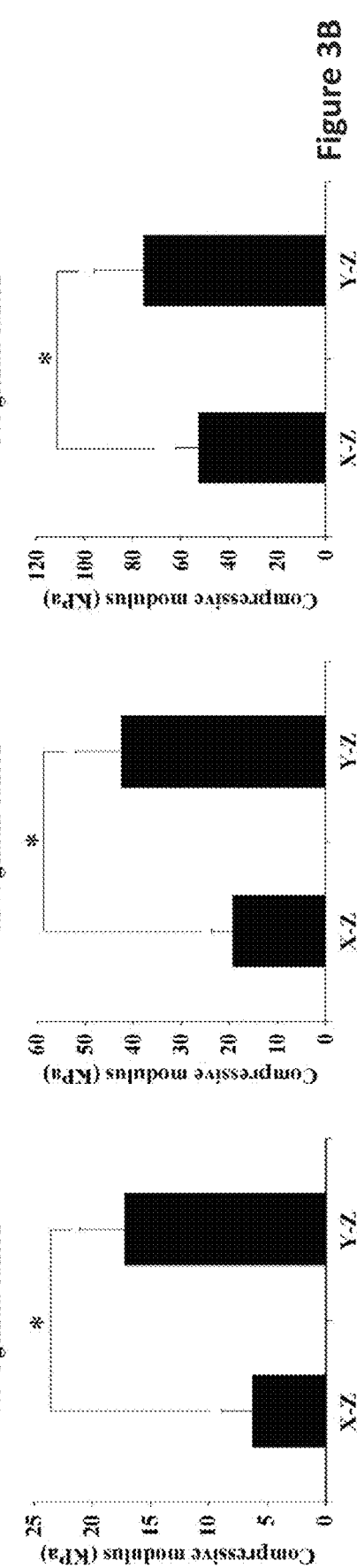
Figure 3A
Figure 3B

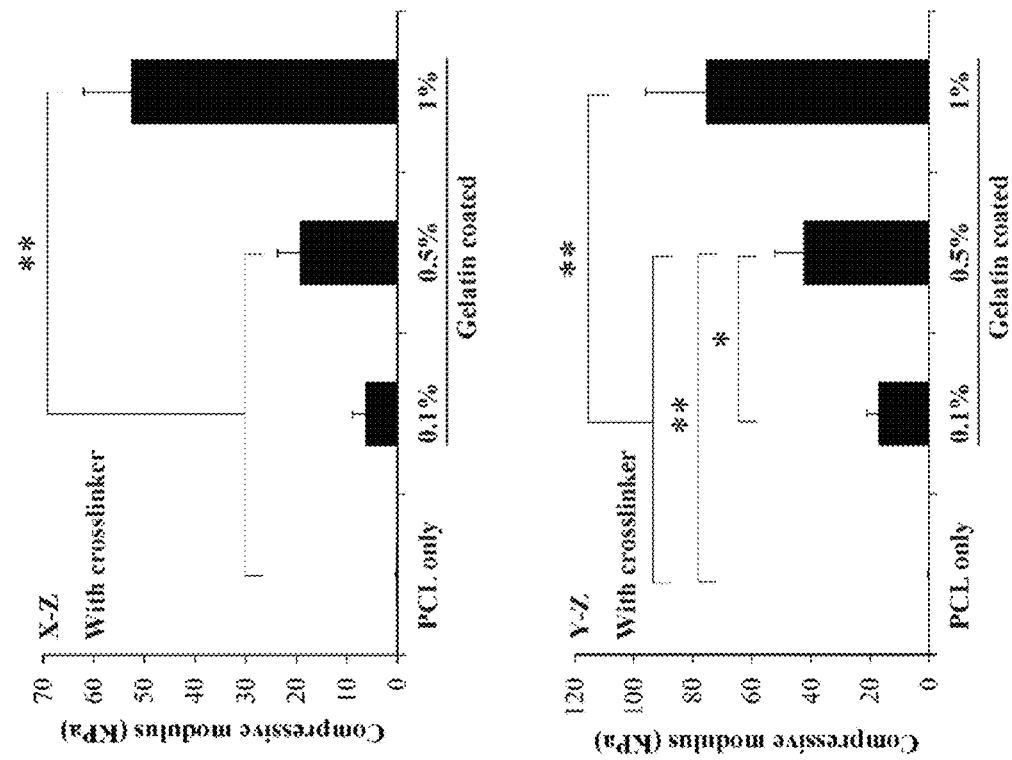
Figure 3C
Figure 3D
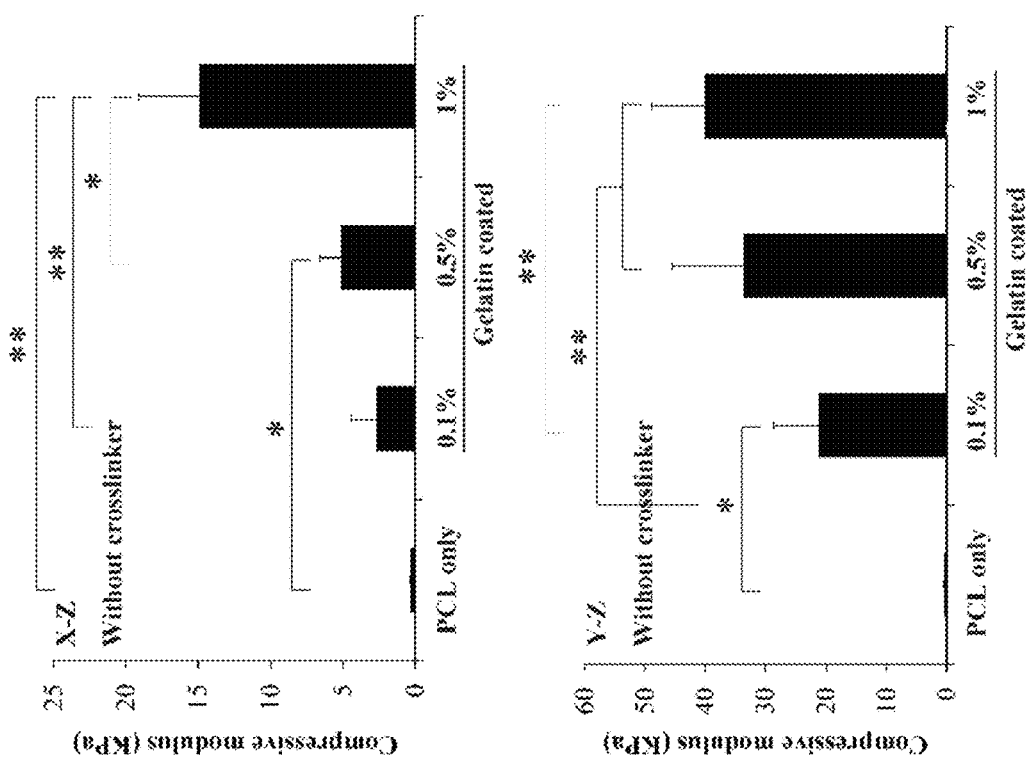

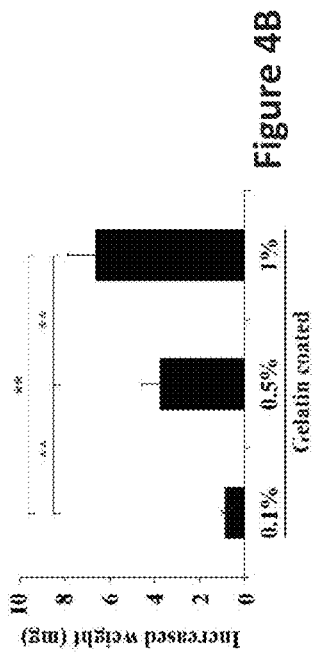
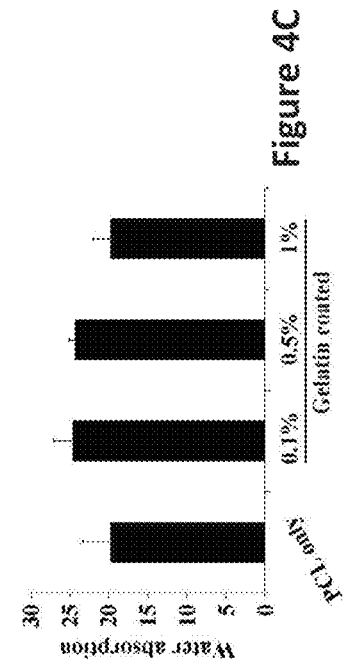
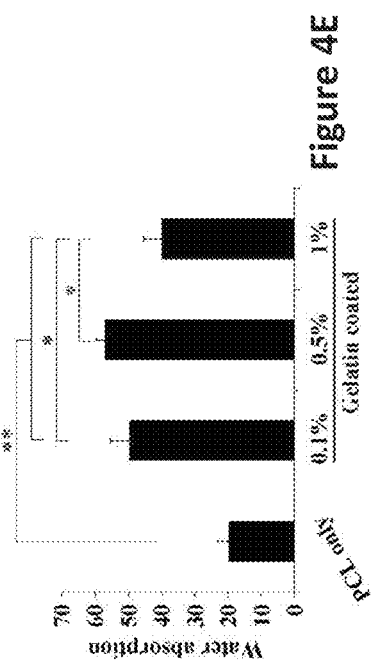
Figure 4A
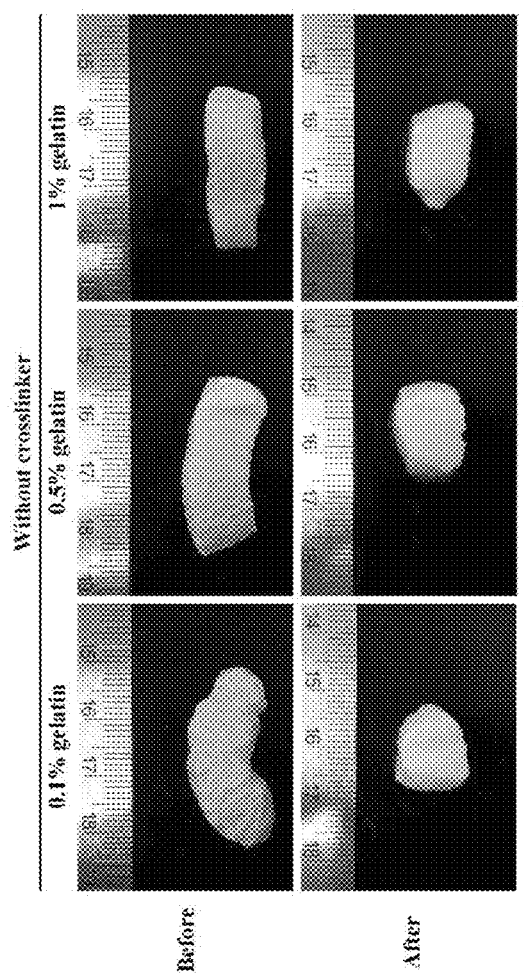
Figure 4D
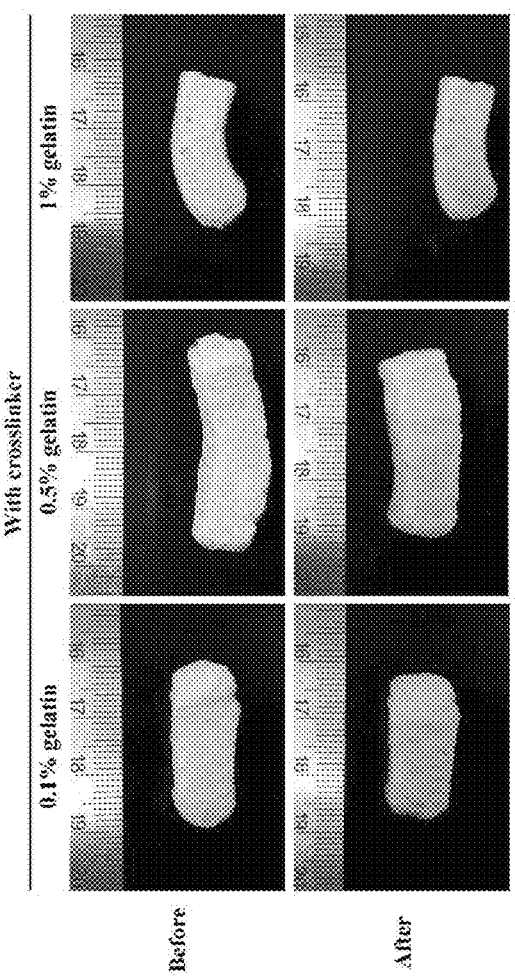

NANOFIBER STRUCTURES AND METHODS OF USE THEREOF

This application is a continuation application of U.S. patent application Ser. No. 16/336,276, filed Mar. 25, 2019, which is a § 371 application of PCT/US2017/053921, filed Sep. 28, 2017, which claims priority under 35 U.S.C. § 119(e) to U.S. Provisional Patent Application No. 62/400,700, filed Sep. 28, 2016. The foregoing applications are incorporated by reference herein.

This invention was made with government support under Grant No. P20 GM103480 and Grant No. U54 GM115458 awarded by the National Institutes of Health (NIH). The government has certain rights in the invention.

FIELD OF THE INVENTION

This application relates to the fields of nanofibers and nanofiber structures. More specifically, this invention provides absorbent nanofiber structures and methods of use thereof.

BACKGROUND OF THE INVENTION

Several publications and patent documents are cited throughout the specification in order to describe the state of the art to which this invention pertains. Each of these citations is incorporated herein by reference as though set forth in full.

According to the National Center for Health Statistics, there were 40 million inpatient surgical procedures performed in the USA in 2000, along with 31.5 million outpatient procedures (Sen et al. (2009) Wound Repair Regen., 17(6):763-771). In addition, there are about 41 million trauma cases each year in the USA with an economic burden of >$670 billion annually (National Trauma Institute. Trauma statistics. nationaltraumainstitute.org). Compositions and methods for the prevention of bleeding and hemorrhaging and for would healing are needed.

SUMMARY OF THE INVENTION

In accordance with the instant invention, nanofiber/nanofibrous structures are provided. In a particular embodiment, the nanofiber/nanofibrous structures comprise an expanded, nanofiber structure comprising a plurality of nanofibers. In a particular embodiment, the nanofiber structure has been expanded by exposure to gas bubbles. The gas bubbles may be generated by a chemical reaction and/or physical means. In a particular embodiment, the gas bubbles are generated as a product of a chemical reaction (e.g., the hydrolysis of sodium borohydride). The nanofiber structure may comprise a plurality of nanofibers (e.g., uniaxially-aligned, random, entangled, and/or electrospun fibers) prior to exposure to the gas bubbles. The nanofiber structure may also comprise a coating of a material that enhances water absorption, such as gelatin. In a particular embodiment, the coating material is a hydrogel. In a particular embodiment, the coating material is gelatin. In a particular embodiment, the nanofiber structure is crosslinked. The nanofiber structure may also comprise an agent or compound such as a therapeutic agent. Nanofiber structures may be bundled with hydrophilic nanofibers (e.g., hydrophilic polymers such as polyvinylpyrrolidone (PVP) or polyethylene oxide (PEO)).

In accordance with another aspect of the instant invention, methods of using the nanofiber structures are provided. For example, the nanofiber structures may be used to inhibit bleeding, enhance wound healing, and/or promote tissue regeneration.

BRIEF DESCRIPTION OF THE DRAWINGS

FIG. 1A provides a schematic illustrating the expansion of nanofiber scaffolds. FIG. 1B provides photographs and scanning electron microscope (SEM) images of nanofiber scaffolds before and after expansion. FIG. 1C provides photographs and SEM images of expanded nanofiber scaffolds (Y-Z and X-Z planes). FIG. 1D provides a graph of the compressive modulus of expanded scaffolds.

FIG. 2A provides images of gelatin sponges (0.1%, 0.5%, or 1.0% gelatin) without crosslinking before and after immersing in water. FIG. 2B provides images of expanded PCL nanofiber scaffolds before and after immersing in water. FIG. 2C provides a graph of the water absorption of expanded PCL nanofiber scaffolds and gelatin sponges without crosslinking. FIG. 2D provides images of gelatin sponges (0.1%, 0.5%, or 1.0% gelatin) with crosslinking before and after immersing in water. FIG. 2E provides a graph of the water absorption (%) of expanded PCL nanofiber scaffolds and gelatin sponges with crosslinking.

FIG. 3A shows the compressive modulus of gelatin sponges (0.1%, 0.5%, or 1.0% gelatin) without crosslinking. FIG. 3B shows the compressive modulus of gelatin sponges (0.1%, 0.5%, or 1.0% gelatin) with crosslinking. FIG. 3C shows the compressive modulus (X-Z) of expanded PCL nanofiber scaffolds without and with gelatin coating and with and without crosslinking. FIG. 3D shows the compressive modulus (Y-Z) of expanded PCL nanofiber scaffolds without and with gelatin coating and with and without crosslinking.

FIG. 4A provides images of expanded PCL nanofiber scaffolds coated with gelatin and without crosslinking. FIG. 4B provides a graph showing the increased weights of PCL nanofiber scaffolds after coating with gelatin. FIG. 4C provides a graph of the water absorption of expanded PCL nanofiber scaffolds without and with gelatin coating and without crosslinking. FIG. 4D provides images of expanded PCL nanofiber scaffolds coated with gelatin and with crosslinking. FIG. 4E provides a graph of the water absorption of expanded PCL nanofiber scaffolds without and with gelatin coating and with crosslinking.

DETAILED DESCRIPTION OF THE INVENTION

Figure 4F:
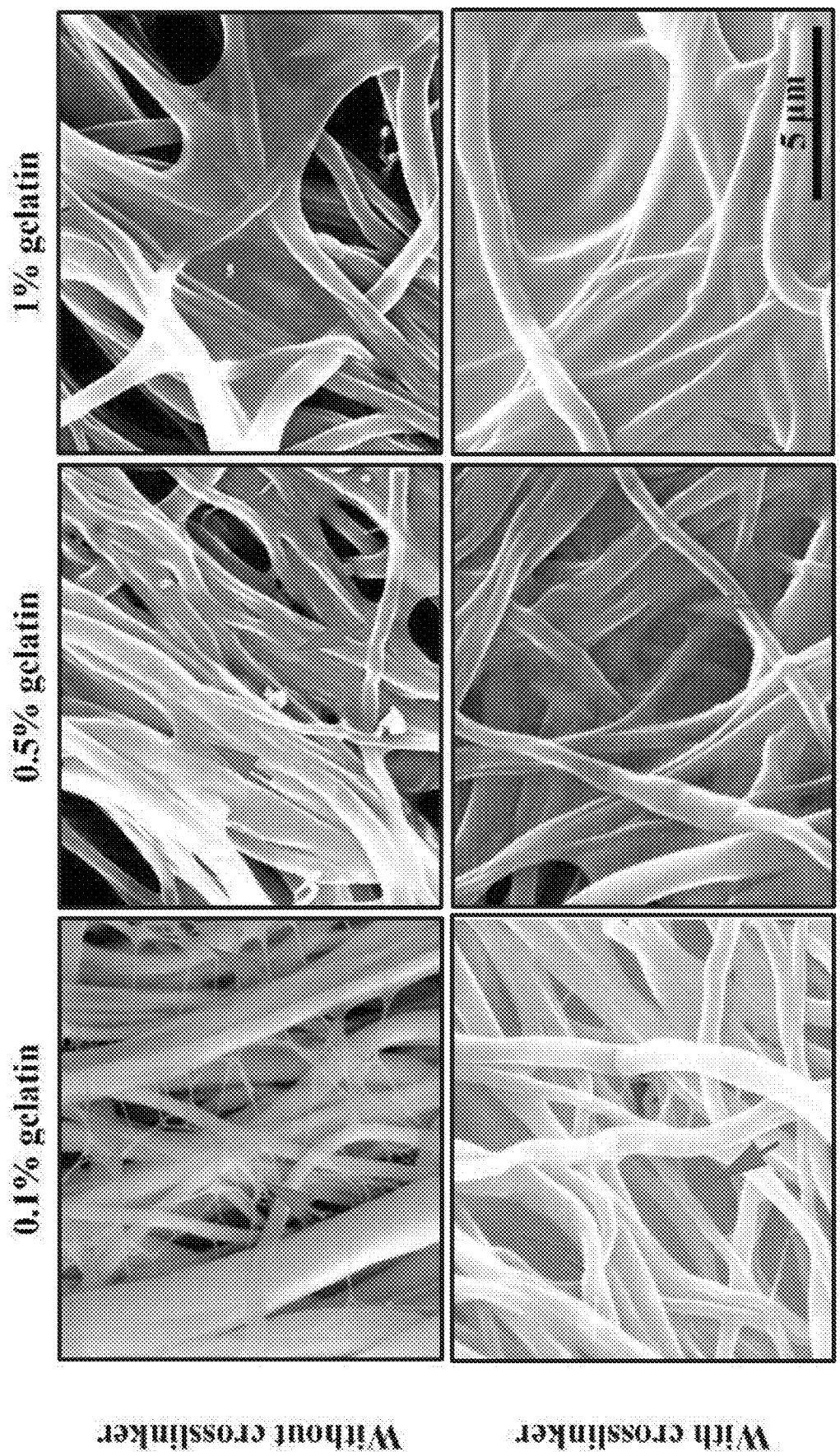
FIG. 4F provides SEM images of expanded PCL nanofiber scaffolds after gelatin coating without and with crosslinking.
Figure 5B:
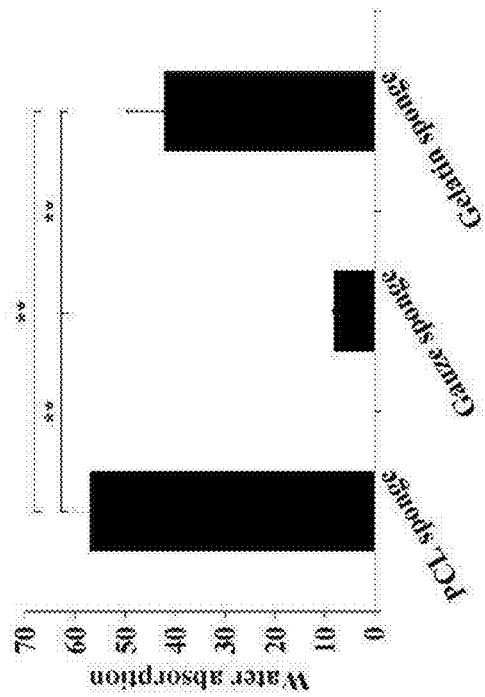
FIG. 5B provides a graph of the water absorption of expanded PCL nanofiber scaffolds coated with 0.5% gelatin, gauze, and gelatin surgical foam.
Figure 5D:
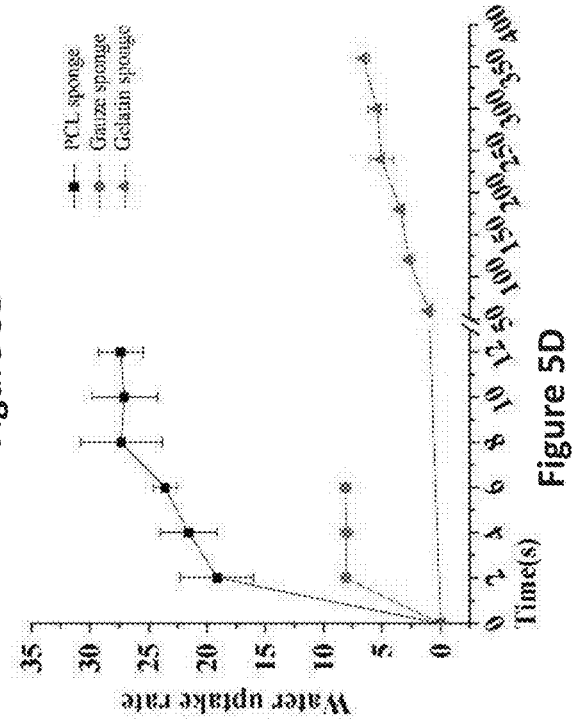
FIG. 5D provides a graph of the water uptake rate (% per second) for expanded PCL nanofiber scaffolds coated with 0.5% gelatin, gauze, and gelatin surgical foam.
Figure 5A:
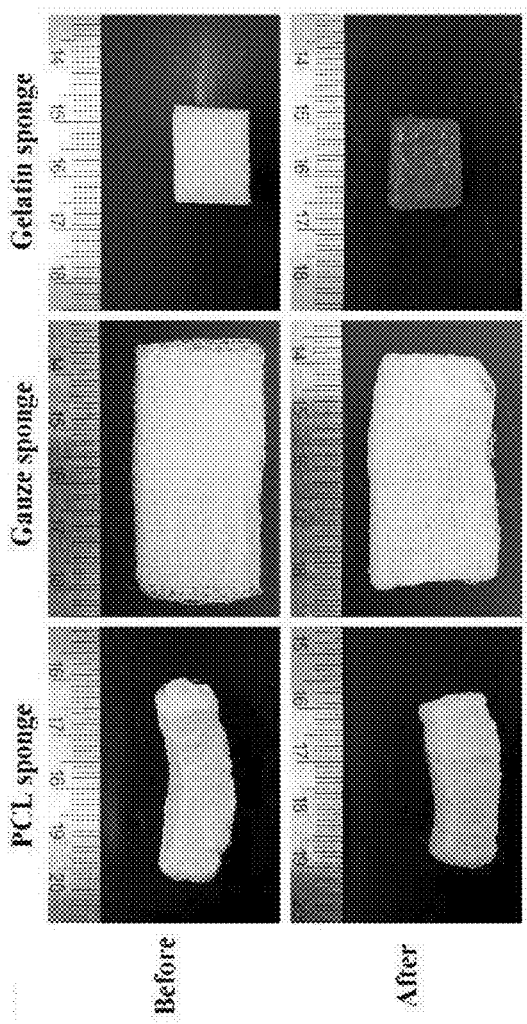
FIG. 5A provides images of expanded PCL nanofiber scaffolds coated with 0.5% gelatin, gauze, and gelatin surgical foam before and after immersing in water.
Figure 5C:
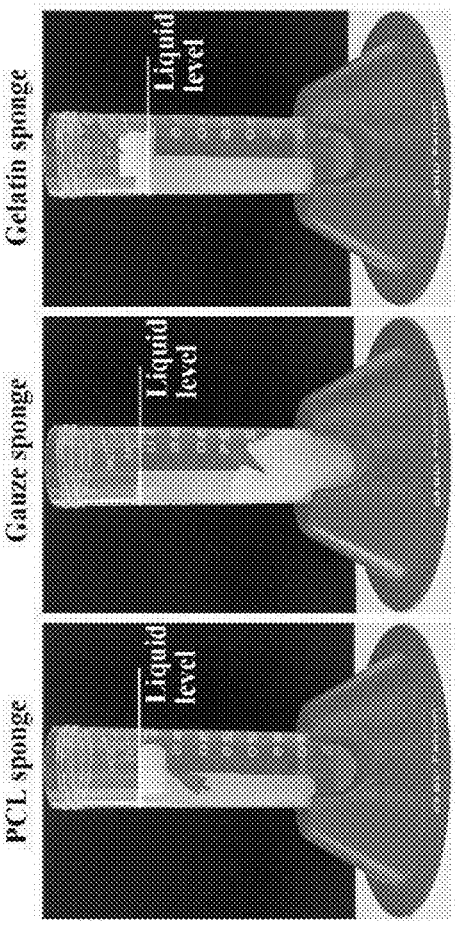
FIG. 5C provides images of expanded PCL nanofiber scaffolds coated with 0.5% gelatin, gauze, and gelatin surgical foam in water.
Figure 5F:
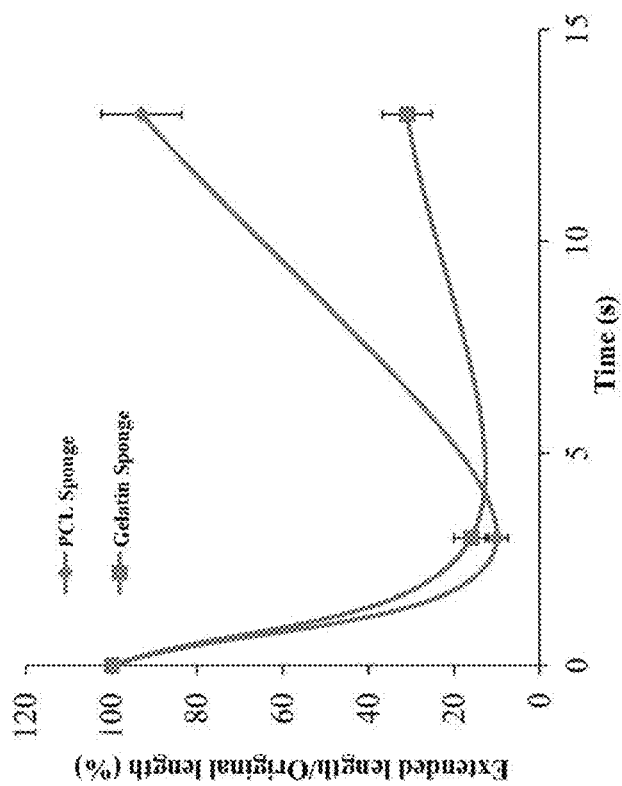
FIG. 5F provides a graph of the length recovery of expanded PCL nanofiber scaffolds coated with 0.5% gelatin and gelatin surgical foam.
Figure 5E:
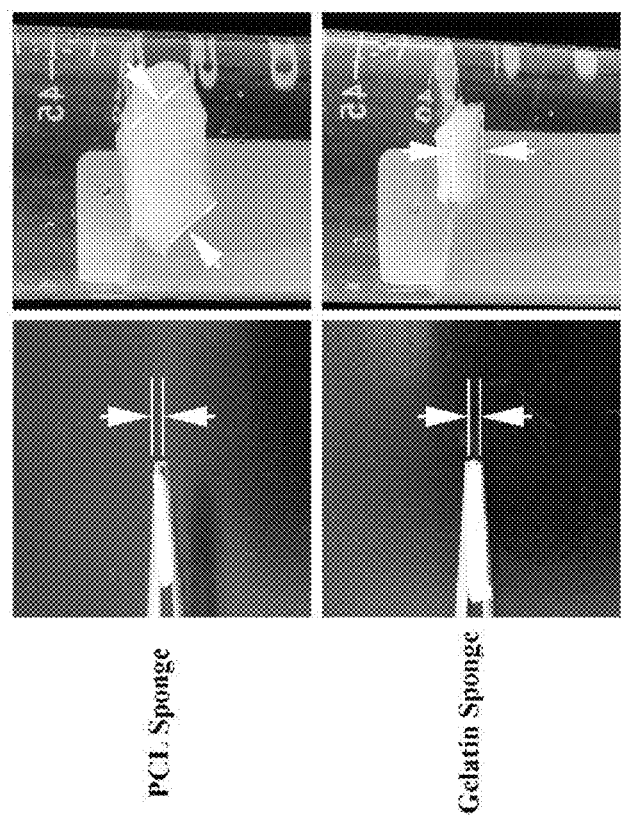
FIG. 5E provides images of the shape recovery of expanded PCL nanofiber scaffolds coated with 0.5% gelatin and gelatin surgical foam after squeezing.

Electrospun nanofibers have shown great potential as scaffolds for regenerative medicine because of its biomimicry. However, traditional two-dimensional electrospun nanofiber mats inhibit their applications because of the dense structure and lack of effective cell infiltration as well as a lack of oxygen and nutrient diffusion. Previous methods used to increase the porosity of the nanofiber scaffolds mainly include ultrasonication, increasing fiber diameter, and selective removal of sacrificial fiber (Lee et al. (2011) Tissue Eng. Part A., 17:2695-702; Pham et al. (2006) Biomacromolecules 7:2796-805; Baer et al. (2008) Biomaterials 29:2348-58; Kidoaki et al. (2005) Biomaterials 26:37-46; Yang et al. (2009) Tissue Eng. A., 15:945-56; Zhou et al. (2006) Polymer 47:7497-505; Brown et al. (2011) Adv. Mater., 23:5651-7; Bkakeney et al. (2011) Biomaterials 32(6):1583-90; Zhang et al. (2007) Adv. Mater., 19:3664-7; Xie et al. (2011) Small 7:293-7; Thandayamoorthy et al. (2006) J. Appl. Polym. Sci., 101:3121-4; Yan et al. (2011) Langmuir 27:4285-9; Xie et al. (2012) Adv. Healthcare Mater., 1:674-8; Lee et al. (2010) Tissue Eng. C. Methods 17:651-61). These technologies, however, are still associated with limited porosity, inefficiencies in production, complex methods, time consuming processes, and a requirement for special costly equipment.

Herein, expanded electrospun nanofiber structures/scaffolds, particularly via a modified gas-foaming technique, and methods of use thereof are provided. Expanded nanofiber structures/scaffolds possess significantly higher porosity than traditional two-dimensional nanofiber membranes, while simultaneously maintaining nanotopographic cues. The distributions of gap widths and layer thicknesses are directly dependent on the processing time of nanofiber mats within the gas bubble forming solution. As seen herein, the expanded nanofiber structure/scaffolds of the instant invention possess superior properties with regard to inhibiting and/or preventing bleeding and/or hemorrhaging.

In accordance with the instant invention, nanofiber structures (sometimes referred to as scaffolds or nanofibrous herein) are provided. The nanofibers of the instant invention can be fabricated by any method. In a particular embodiment, the nanofiber structures comprise electrospun nanofibers. In a particular embodiment, the nanofiber structure comprises uniaxially aligned fibers, random fibers, and/or entangled fibers. While the application generally describes nanofiber (fibers having a diameter less than about 1 µm (e.g., average diameter)) structures and the synthesis of three-dimensional nanofibrous structures, the instant invention also encompasses microfiber (fibers having a diameter greater than about 1 µm (e.g., average diameter)) structures and the synthesis of three-dimensional microfibrous structures. In a particular embodiment, the nanofibrous structures are expanded, such as produced by a gas-foaming technique. For example, nanofiber structures (e.g., mats) may be expanded by being placed into conditions (e.g., submerged or immersed in a liquid) wherein gas bubbles are generated for various amounts of time. The nanofiber structure may be cut or shaped prior to expansion. The nanofiber structure may be crosslinked.

The nanofibers of the instant invention may comprise any polymer. In a particular embodiment, the polymer is biocompatible. The polymer may be biodegradable or non-biodegradable. The polymer may by hydrophobic, hydrophilic, or amphiphilic. In a particular embodiment, the polymer is hydrophobic. The polymer may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyperbranched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini.

Examples of hydrophobic polymers include, without limitation: polyvinyl alcohol (PVA), poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(2-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly(caprolactonefumarate), poly(1,2-butylene oxide), poly(n-butylene oxide), poly(ethyleneimine), poly(tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO. Amphiphilic copolymers may comprise a hydrophilic polymer (e.g., segment) and a hydrophobic polymer (e.g., segment) from those listed above (e.g., gelatin/PVA, PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers particularly useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen type I, II, and/or III, elastin, hyaluronic acid, cellulose, silk fibroin, phospholipids (Lecithin), fibrinogen, hemoglobin, fibrous calf thymus Na-DNA, virus M13 viruses), synthetic polymers (e.g., PLGA, PLA, PCL, PHBV, PDO, PGA, PLCL, PLLA-DLA, PEUU, cellulose acetate, PEG-b-PLA, EVOH, PVA, PEO, PVP), blended (e.g., PLA/PCL, gelatin/PVA, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA). In a particular embodiment, the nanofiber comprises polymethacrylate, poly vinyl phenol, polyvinylchloride, cellulose, polyvinyl alcohol, polyacrylamide, PLGA, collagen, polycaprolactone, polyurethanes, polyvinyl fluoride, polyamide, silk, nylon, polybennzimidazole, polycarbonate, polyacrylonitrile, polyvinyl alcohol, polylactic acid, polyethylene-co-vinyl acetate, polyethylene oxide, polyaniline, polystyrene, polyvinylcarbazole, polyethylene terephthalate, polyacrylic acid-polypyrene methanol, poly(2-hydroxyethyl methacrylate), polyether imide, polyethylene gricol, polyethylene glycol, poly(ethylene-co-vinyl alcohol), polyacrylnitrile, polyvinyl pyrrolidone, polymetha-phenylene isophthalamide, and/or combinations of two or more polymers. In a particular embodiment, the polymer is polycaprolactone (PCL). In a particular embodiment, the polymer is a biodegradable polymer.

In a particular embodiment, the nanofiber structures comprise a material that enhances the nanofiber structure's ability to absorb fluids, particularly aqueous solutions, more particularly blood. In a particular embodiment, the nanofiber structures are coated with the material which enhances the absorption properties. The term "coat" refers to a layer of a substance/material on the surface of a structure. Coatings may, but need not, also impregnate the nanofiber structure. Further, while a coating may cover 100% of the nanofiber structure, a coating may also cover less than 100% of the surface of the nanofiber structure (e.g., at least about 75%, at least about 80%, at least about 85%, at least about 90%, at least about 95%, at least about 98%, or more the surface may be coated). Coating materials which enhance the absorption properties of the expanded nanofiber structures include, without limitation: gelatin, chitosan, collagen, starch, pectin, cellulose, methylcellulose, sodium polyacrylate, starch-acrylonitrile co-polymers, other natural or synthetic hydrogels, and derivatives thereof (e.g., del Valle et al., Gels (2017) 3:27). In a particular embodiment, the coating material is a hydrogel (e.g., a polymer matrix able to retain water, particularly large amounts of water, in a swollen state). In a particular embodiment, the coating material is gelatin. In a particular embodiment, the expanded nanofiber structures are coated with about 0.05% to about 10% coating material (e.g., gelatin), particularly about 0.1% to about 10% coating material (e.g., gelatin) or about 0.1% to about 1% coating material (e.g., gelatin). In a particular embodiment, the coating material (e.g., hydrogel) is cross-linked.

As stated hereinabove, the nanofiber structures of the instant invention are expanded. Electrospun nanofibers are usually deposited on a substrate to form a nanofiber mat. However, the nanofiber mats are often dense and hard. These nanofiber mats can be expanded by making use of bubbles (e.g., generated by chemical reactions in an aqueous solution (e.g., a gas foaming technique)). The gas bubbles may be formed by any chemical reaction and/or physical mean. For example, the bubbles may be generated, without limitation, using a gas-production chemical reactions; by dissolved gas in a liquid under a high pressure and/or a low temperature; pressurized gas (e.g., CO$_2$) liquid; and/or physical means (e.g., laser (e.g., pulsed laser), acoustic induced, or flow induced). In a particular embodiment, the nanofiber structure is submerged or immersed in a bubble/gas producing chemical reaction or physical manipulation. Generally, the longer the exposure to the bubbles, the greater the thickness and porosity of the nanofiber structure increases.

The gas bubbles of the instant invention can be made by any method known in the art. The bubbles may be generated, for example, by chemical reactions or by physical approaches. In a particular embodiment, the chemical reaction or physical manipulation does not damage or alter or does not substantially damage or alter the nanofibers (e.g., the nanofibers are inert within the chemical reaction and not chemically modified). As explained hereinabove, the nanofiber structure may be submerged or immersed in a liquid comprising the reagents of the bubble-generating chemical reaction. Examples of chemical reactions that generate bubbles include, without limitation:

$$NaBH_4 + 2H_2O = NaBO_2 + 4H_2$$

$$NaBH_4 + 4H_2O = 4H_2(g) + H_3BO_3 + NaOH$$

$$HCO_3^- + H^+ = CO_2 + H_2O$$

$$NH_4^+ + NO_2^- \longrightarrow N_2 + 2H_2O$$

$$H_2CO_3 = H_2O + CO_2$$

$$2H^+ + S^{2-} = H_2S$$

$$2H_2O_2 = O_2 + 2H_2O$$

$$3HNO_2 = 2NO + HNO_3 + H_2O$$

$$HO_2CCH_2COCH_2CO_2H = 2CO_2 + CH_3COCH_3$$

$$2H_2O_2 = 2H_2 + O_2$$

$$CaC_2 + H_2O = C_2H_2$$

$$Zn + 2HCl = H_2 + ZnCl_2$$

$$2KMnO_4 + 16HCl = 2KCl + 2MnCl2 + H_2O + 5Cl_2$$

In a particular embodiment, the chemical reaction is the hydrolysis of $NaBH_4$ (e.g., $NaBH_4 + 2H_2O = NaBO_2 + 4H_2$). In a particular embodiment, $CO_2$ gas bubbles (generated chemically or physically (see below)) are used for hydrophilic polymers.

Examples of physical approaches for generating bubbles of the instant invention include, without limitation: 1) create high pressure (fill gas)/heat in a sealed chamber and suddenly reduce pressure; 2) dissolve gas in liquid/water in high pressure and reduce pressure to release gas bubbles; 3) use supercritical fluids (reduce pressure) like supercritical $CO_2$; 4) use gas liquid (then reduce pressure) (e.g., liquid $CO_2$, liquid propane and isobutane); 5) fluid flow; 6) apply acoustic energy or ultrasound to liquid/water; 7) apply a laser (e.g., to a liquid or water); 8) boiling; 9) reduce pressure boiling (e.g., with ethanol); and 10) apply radiation (e.g., ionizing radiation on liquid or water). The nanofiber structure may be submerged or immersed in a liquid of the bubble-generating physical manipulation.

The nanofiber structure may also be expanded within a mold (e.g., a metal, plastic, or other material that does not expand in the presence of gas bubbles) such that the expanded nanofiber structure forms a desired shape (e.g., pads, tubes, beads, etc.). The nanofiber structures of the instant invention may also be manipulated after expansion to form a desired shape (e.g., pads, tubes, beads, etc.). The nanofiber structure may be treated with air plasma prior to exposure to gas bubbles (e.g., to increase hydrophilicity).

After exposure to the bubbles, the nanofiber structure may be washed or rinsed in water and/or a desired carrier or buffer (e.g., a pharmaceutically or biologically acceptable carrier). Trapped gas bubbles may be removed by applying a vacuum to the nanofiber structure. For example, the expanded nanofiber structure may be submerged or immersed in a liquid (e.g., water and/or a desired carrier or buffer) and a vacuum may be applied to rapidly remove the gas bubbles. After expansion (e.g., after rinsing and removal of trapped gas), the nanofiber structures may be lyophilized and/or freeze-dried.

The nanofiber structures of the instant invention may comprise or encapsulate at least one agent, particularly a therapeutic agent (e.g., analgesic, a therapeutic agent, drug, bioactive agent, growth factor, signaling molecule, cytokine, antimicrobial (e.g., antibacterial, antibiotic, antiviral, and/or antifungal), blood clotting agent, factor, or protein, etc.). The agent may be added to the nanofiber structures during synthesis and/or after synthesis. The agent may be conjugated to the nanofiber structure and/or coating material, encapsulated by the nanofiber structure, and/or coated on the nanofiber structure (e.g., with, underneath, and/or on top of the coating that enhances the nanofiber structure's ability to absorb fluids). In a particular embodiment, the agent is not directly conjugated to the nanofiber structure. In a particular embodiment, the agents are administered with but not incorporated into the expanded nanofiber structures.

In a particular embodiment, the agent is an antimicrobial, particularly an antimicrobial. In a particular embodiment, the agent is a blood clotting agent. Examples of blood clotting agents include, without limitation: antifibrinolytic drugs (e.g., aprotinin, tranexamic acid (TXA), epsilon-aminocaproic acid and aminomethylbenzoic acid), blood coagulation factors (e.g., fibrinogen (Factor I), thrombin (Factor II), crosslinking factor (Factor XIII), Factor VIII, Factor X, Factor IX, etc.), vitamin K (e.g., phytomenadione), platelets, lyophilized platelet products, chitin, and chitosan. In a particular embodiment, the agent enhances wound healing and/or enhances tissue regeneration (e.g., bone, tendon, cartilage, skin, nerve, and/or blood vessel). Such agents include, for example, growth factors and small molecules. Growth factors include, without limitation: platelet derived growth factor (PDGF), vascular endothelial growth factor (VEGF), epidermal growth factor (EGF), fibroblast growth factor (FGF, multiple isotypes; e.g. basic fibroblast growth factor (bFGF)), insulin-like growth factor (IGF-1 and/or IGF-2), bone morphogenetic protein (e.g., BMP-2, BMP-7, BMP-12, BMP-9), transforming growth factor (e.g., TGFβ, TGFβ3), nerve growth factor (NGF), neurotrophic factor, glial cell-derived neurotrophic factor (GDNF), and/or keratinocyte growth factor (KGF). Small molecules include, without limitation, sirmstatin, kartogenin, retinoic acid, paclitaxel, vitamin D3, etc.

In accordance with the instant invention, the nanofiber structures may be used in the treatment, inhibition, and/or prevention of bleeding and/or hemorrhaging, inducing and/or improving/enhancing wound healing, and inducing and/or improving/enhancing tissue regeneration. The nanofiber structures of the present invention can be used for the treatment, inhibition, and/or prevention of any injury or wound, particularly one associated with or involving bleeding. For example, the nanofiber structures can be used to treat, inhibit, and/or prevent bleeding and/or hemorrhage associated with surgery (including non-elective (e.g., emergency) surgical procedures or elective surgical procedures). Elective surgical procedures include, without limitation: liver resection, partial nephrectomy, cholecystectomy, vascular suture line reinforcement and neurosurgical procedures. Non-elective surgical procedures include, without limitation: severe epistaxis, splenic injury, liver fracture, cavitary wounds, minor cuts, punctures, gunshot wounds, and shrapnel wounds. In a particular embodiment, the nanofiber structures of the instant invention can be used to treat, inhibit, and/or prevent bleeding associated with the menstrual cycle (e.g., the nanofiber structures may be included in feminine hygiene products such as tampons and pads). The nanofiber structures of the present invention can also be incorporated into delivery devices (e.g., a syringe) that allow for their injection/delivery directly into a desired location (e.g., a wound such as a gunshot wound). The nanofiber structures also may be delivered directly into a cavity (such as the peritoneal cavity) using a pressurized cannula (e.g., for prehospital treatment of life-threatening intraabdominal hemorrhage secondary to blunt or penetrating trauma, in either military or civilian scenarios).

In accordance with the instant invention, methods for the inhibition, prevention, and/or treatment of bleeding and/or hemorrhaging in a subject in need thereof are provided. Methods for inducing and/or improving/enhancing wound healing in a subject are also provided. Methods of inducing and/or improving/enhancing tissue regeneration (e.g., blood vessel growth, neural tissue regeneration, and bone regeneration) in a subject are also encompassed by the instant invention. The methods of the instant invention comprise administering or applying a nanofiber structure of the instant invention to the subject (e.g., at the site of bleeding, at or in a wound, etc.). In a particular embodiment, the method comprises administering a nanofiber structure comprising an agent as described hereinabove. In a particular embodiment, the method comprises administering a nanofiber structure to the subject and an agent as described hereinabove (i.e., the agent is not contained within the nanofiber structure). When administered separately, the nanofiber structure may be administered simultaneously and/or sequentially with the agent. The methods may comprise the administration of one or more nanofiber structures. When more than one nanofiber structure is administered, the nanofiber structures may be administered simultaneously and/or sequentially.

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "antibiotic" refers to antibacterial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

As used herein, the term "small molecule" refers to a substance or compound that has a relatively low molecular weight (e.g., less than 2,000). Typically, small molecules are organic, but are not proteins, polypeptides, or nucleic acids.

The term "hydrogel" refers to a water-swellable, insoluble polymeric matrix (e.g., hydrophilic polymers) comprising a network of macromolecules, optionally crosslinked, that can absorb water to form a gel.

The term "crosslink" refers to a bond or chain of atoms attached between and linking two different molecules (e.g., polymer chains). The term "crosslinker" refers to a molecule capable of forming a covalent linkage between compounds. Crosslinkers are well known in the art (e.g., formaldehyde, paraformaldehyde, acetaldehyde, glutaraldehyde, etc.). The crosslinker may be a bifunctional, trifunctional, or multifunctional crosslinking reagent. In a particular embodiment, the crosslinker is paraformaldehyde.

The following example is provided to illustrate certain embodiments of the invention. It is not intended to limit the invention in any way.

EXAMPLE

Fabrication of Electrospun Nanofiber Scaffolds

Nanofibers were produced utilizing a standard electrospinning setup following established protocols (Xie et al. (2009) Biomaterials 30:354-362; Xie et al. (2013) Acta Biomater., 9:5698-5707; Jiang et al. (2015) Pharm. Res., 32:2851-2862). Poly(ε-caprolactone) (PCL; Mw=80 kDa) was dissolved in a solvent mixture consisting of dichloromethane (DCM) and N,N-dimethylformamide (DMF)

with a ratio of 4:1 (v/v) at a concentration of 10% (w/v). PCL solutions were pumped at a flow rate of 0.8 mL/hour using a syringe pump while an electrical potential of 15 kV was applied between the spinneret (a 22-gage needle) and a grounded collector located 20 cm apart from thespinneret. Aligned and random nanofiber mats 1 mm thick were collected on a drum rotating at speeds of 2000 and 100 rpm, respectively. Nanofiber mats were cut in liquid nitrogen to avoid deformation on the edge. Tubular nanofiber scaffolds were fabricated by depositing a 1 mm thick layer of aligned nanofibers followed by a 50 µm thick layer of random nanofibers. To fabricate tubular scaffolds made of random nanofibers in the outer layer and longitudinally aligned nanofibers, the obtained fiber mats were manually rolled overin two different directions (parallel and vertical) and sealed the edges with a 30% PCL DCM solution to form dual-layered tubular nanofiber scaffolds composed of random nanofibers in the outer layer and longitudinally or circumferentially aligned nanofibers in the inner layer. To generate gas bubbles in the solution, the following chemical reaction was chosen for a "proof-of-concept":

$$NaBH_4 + 2H_2O \rightarrow NaBO_2 + 4H_2\uparrow$$

$NaBH_4$ has been extensively investigated for $H_2$ storage and generation because of its relatively high hydrogen content (10.9%) and a controllable hydrolysis reaction (Ye et al. (2007) J. Power Sources 164:544-548; Liu et al. (2009) J. Power Sources 187:527-534). PCL nanofiber mats (1 cm×1 cm×1 mm) were employed to investigate the effects of the expansion process. PCL nanofiber mats were immersed in 40 mL fresh prepared $NaBH_4$ solutions and shaken at 50 rpm for varying lengths of time (0 minutes, 20 minutes, 1, 2, 4, and 24 hours) at 21° C. $NaBH_4$ solutions were prepared at 0.01, 0.1, and 1 M. Sample thickness was measured at 0 minutes, 20 minutes, 1 hour, 2 hours, 4 hours, and 24 hours using a vernier caliper while sample morphology was documented via a digital camera. Following expansion, the $NaBH_4$ solution was discarded and the expanded PCL nanofiber scaffolds were gently transferred into a beaker and rinsed three times with deionized water. To remove trapped gas bubbles, the expanded scaffolds were immersed in water and exposed to a vacuum (~200 Pa) for 3 seconds. Finally, expanded nanofiber scaffolds were rinsed additional three times with deionized water.

Characterization of Nanofiber Scaffolds

Tubular nanofiber scaffolds were made of random fibers in the outer layer and aligned fibers in the inner layer as mentioned above. Tubular scaffolds were expanded in the 1 M $NaBH_4$ solution similar to planar nanofiber mats. The inner and outer diameters of the tubular scaffolds were measured using a vernier caliper and digital photographs were taken at 0 minutes, 20 minutes, 1 hour, 2 hours, 4 hours, and 24 hours. SEM was used to examine fiber architectures upon cross sections of tubular scaffolds before and after the expansion procedure. The mean thickness of nanofiber mats and diameter of tubular scaffolds were reported across at least three independent experiments. The porosity of nanofiber scaffolds was calculated according to the volume change of nanofiber scaffolds pre- and post-expansion. Porosity was calculated using the following equation $$\varepsilon = [(V-V_0)/V]100\%$$

where $\varepsilon$ is porosity, $V=L$ (length)$\times W$ (width)$\times T$ (thickness) is the volume of PCL nanofiber scaffold, $V_0=((m_0)/(\rho_0))$ is the calculated volume of bulk PCL material, $m_0$ is the mass of bulk PCL material, and $\rho_0$ is the density of bulk PCL materials.

PCL nanofiber mats were embedded in deionized water and frozen at −20° C. pre- and post-expansion. Cross sections of frozen nanofiber scaffolds were obtained using a cryostat and freeze-dried. SEM (FEI, Quanta 200, Oregon) was used to characterize nanofiber morphologies and architecture within cross sections of scaffolds. To avoid charging, nanofiber samples were fixed on a metallic stud with double-sided conductive tape and sputter-coated with platinum for 4 minutes under vacuum at a current intensity of 10 mA. SEM images were acquired at an accelerating voltage of 30 kV. Gap distances and layer thicknesses observed in nanofiber scaffolds pre- and post-expansion using 1 M $NaBH_4$ for 20 minutes and 24 hours were measured based on SEM images by the ImageJ software. At least 250 gaps or layers have been analyzed.

Mechanical properties of nanofiber scaffolds pre-expansion (1 cm×1 cm×1 mm) and post-expansion (1 cm×1 cm×1 cm) were measured. Nanofiber samples were mounted between two steel grips and two 1.5 cm diameter glass coverslips in order to measure tensile and compressive modulus, respectively. After equilibration, the trigger for tensile and compressive test and rate was set at 750 µN and $5.0 \times 10^{-3}$ s$^{-1}$. The resulting force (F) and length changing ($\Delta L$) were recorded by the loading cell and digital data acquisition system. Engineering stress ($\sigma = F/A$) and engineering strain ($\delta = \Delta L/L_0$) were calculated by dividing the resulting force (F) and length changing ($\Delta L$) over the cross-sectional area (A) and initial length ($L_0$). Young's modulus was given by $E = \sigma/\varepsilon$. Testing ceased when the maximum force reached 500 mN or the samples broke. Testing of aligned PCL nanofiber scaffolds post-expansion, including maximum stress, ultimate tensile stress, and ultimate tensile strain, was completed parallel to the axis of fiber alignment (y axis) and orthogonal to the axis of fiber alignment (z axis). Testing of random PCL nanofiber scaffolds post-expansion, including the maximum stress, ultimate tensile stress, and ultimate tensile strain, was completed orthogonally to the axis of fiber alignment (z axis). Mechanical testing was performed on at least five independent samples per material/condition.

Animal Studies

A stellate injury to the liver dome was performed as described (Yanala et al., PLOS ONE (2014) 9(9):e108293). Briefly, domestic swine (castrated males, age 3 months) were purchased from the Agricultural Research and Development Center (Mead, NE) of the University of Nebraska-Lincoln. Subjects underwent an acclimatization period of at least four days, during which time they underwent veterinary examination and daily observation to confirm good health. Subjects were fed ad lib with corn-soybean meal supplemented with vitamins, and maintained in specific-pathogen free (SPF) conditions. Each subject was fasted for 12 hours before the surgical procedure, but with free access to water.

Animal preparation was performed as described (Carlson et al. (2014) J. Surg. Res., 187:334-342). Briefly, each subject was premedicated with a single 3 mL intramuscular (IM) injection containing 150 mg Telazol (tiletamine hydrochloride and zolazepam hydrochloride, 1:1 by weight; Fort Dodge Animal Health, New York, NY), 90 mg ketamine, and 90 mg xylazine (drugs were combined in saline immediately prior to injection). After premedication each subject was weighed, and then intravenous line was established in an auricular vein. Oral endotracheal intubation (7.5 mm internal diameter cuffed tube) was performed, and anesthesia was maintained with 0.5-1.5% isoflurane using a Matrx Model 3000 Veterinary Anesthesia Ventilator (Midmark Corp., Versailles, OH). Mechanical ventilation was maintained at 12-15 breaths per minute, with a tidal volume of 10-15 mL/kg, in order to keep the end-tidal $pCO_2$ at 30-40 mm Hg. A heating pad was placed under each subject to support body temperature. A cutdown in the right neck (along the medial edge of the sternocleidomastoid muscle) was performed, and then a carotid arterial catheter (20 gauge) was inserted for pressure monitoring and blood sampling, followed by a jugular venous catheter (16 gauge) for isotonic fluid administration. Arterial pressure, end-tidal $pCO_2$, rectal temperature, cardiac electrical activity, and pulse oximetry (tongue probe) were continuously recorded with a Bionet BM5 Veterinary Monitor (Bionet America, Inc.; Tustin, CA) interfaced to a laptop computer. Each swine subject was maintained under an appropriate level of isoflurane anesthesia (indicated by absence of the corneal reflex) for the duration of the procedure; prior to euthanasia, the isoflurane was increased.

Upon placement of the arterial line, 20 mL of blood was withdrawn for a serum test set, which included a complete blood count (CBC), protime (PT), partial thromboplastin time (PTT), international normalized ratio (INR), fibrinogen, arterial blood gas analysis (ABG), and thromboelastography (TEG). After completion of the above preparations, a ventral midline laparotomy incision was made through the linea alba, starting at the xiphoid process and extending inferiorly. Just superior to the urethral meatus, this incision was angled to the right in order to avoid the midline penis and urethra (but medial to the nipple line), and then was continued inferiorly down to but not into the right groin. The incision was performed with cautery to control any bleeding points from the musculoaponeurotic layers. Splenectomy then was performed, followed by placement of a cystostomy tube (18 French Foley) in the dome of the urinary bladder, secured with a purse string silk suture. The cystostomy tube exited through a stab incision in the left lower quadrant, and was connected to gravity drainage. The excised spleen was weighed, and then a volume of warm Lactated Ringers (LR; 37° C.) solution equivalent to three-fold the splenic weight was administered through the jugular line, using a rapid infusion pump (Cole-Palmer Masterflex® L/S; Vernon Hills, IL) set at 150 mL/min. An improvised intraabdominal pressure (IAP) monitor (100 mL IV bag) then was placed along the left paracolic gutter; the pressure line of this monitor exited out of the superior end of the laparotomy incision, and was connected to the Bionet monitor (kept level with the subject) for continuous recording of IAP. The IAP monitor was zeroed while the abdominal incision was open.

Prior to injury, any blood loss incurred during the preparation was quantified by weighing tared surgical sponges that were used to absorb lost blood, and then a volume of LR equivalent to three-fold the pre-injury blood loss (typically <50 mL) was given using the infusion pump. Immediate pre-injury vital signs were recorded, the lower half of the midline incision was closed with towel clips, and then the primary injury mechanism was applied.

All injuries were performed in normothermic normovolemic (resuscitated) swine and only one injury was performed per subject. Immediately after injury, the abdominal incision was closed rapidly with towel clips in all subjects. No post-injury treatment (other than the nanofiber scaffolds) was administered.

The porcine normothermic normovolemic stellate liver laceration model was adapted from other descriptions (Carlson et al. (2014) J. Surg. Res., 187:334-342; Holcomb et al. (1999) J. Trauma 46:49-57). A liver laceration was created with a custom-built liver injury clamp (Carlson et al. (2014) J. Surg. Res., 187:334-342), which consisted of metal tines in an X-configuration (5 cm diameter) on one arm of the clamp, and a base plate on the other arm onto which the tines seated. The base plate was placed on the inferior surface of the liver against the quadrate lobe, between the cystic duct and the portal vein. The tines were positioned over the liver dome, directly anterior (within 1 cm) to the vena cava at the base of the left medial hepatic segment. The clamp then was closed, forcing the tines through the liver dome and onto the base plate. The clamp immediately was re-opened, moved 2-3 cm to the right, and then closed again, such that the second clamp strike overlapped ~50% with the first strike.

Results

Electrospun nanofiber mats were successfully expanded in the third dimension after treatment with the $NaBH_4$ aqueous solutions (FIG. 1). The terminal thickness of treated nanofiber mats increased with increasing time in solution and with increasing concentration of $NaBH_4$. For example, the thickness of nanofiber mats increased from 1.1 mm to 35.2 mm after only 24 hour treatment with the 1 M $NaBH_4$ aqueous solution (FIG. 1B). FIG. 1C provides photographs and scanning electron microscope (SEM) images of expanded nanofiber scaffolds (Y-Z and X-Z Planes). FIG. 1D provides a graph of the compressive modulus of expanded scaffolds.

The water absorption for expanded PCL nanofiber scaffolds and gelatin sponges is shown in FIG. 2. It is observed that expanded PCL nanofiber scaffolds can absorb water with 20 times their own weight. The absorbed water for crosslinked gelatin sponges (1%) can reach about 40 times of their own weight. FIG. 2A provides images of gelatin sponges (0.1%, 0.5%, or 1.0% gelatin) without crosslinking before and after immersing in water. FIG. 2B provides images of expanded PCL nanofiber scaffolds before and after immersing in water. FIG. 2C provides a graph of the water absorption of expanded PCL nanofiber scaffolds and gelatin sponges without crosslinking. FIG. 2D provides images of gelatin sponges (0.1%, 0.5%, or 1.0% gelatin) with crosslinking (using paraformaldehyde as a crosslinking agent) before and after immersing in water. FIG. 2E provides a graph of the water absorption of expanded PCL nanofiber scaffolds and gelatin sponges with crosslinking.

Expanded PCL nanofiber scaffolds were then coated with gelatin by immersion in a gelatin solution. The mechanical properties of gelatin sponges, expanded PCL nanofiber scaffolds, and gelatin-coated, expanded PCL nanofiber scaffolds are shown in FIG. 3. FIG. 3A shows the compressive modulus of gelatin sponges (0.1%, 0.5%, or 1.0% gelatin) without crosslinking. FIG. 3B shows the compressive modulus of gelatin sponges (0.1%, 0.5%, or 1.0% gelatin) with crosslinking. FIG. 3C shows the compressive modulus (X-Z) of expanded PCL nanofiber scaffolds without and with gelatin coating and with and without crosslinking. FIG. 3D shows the compressive modulus (Y-Z) of expanded PCL nanofiber scaffolds without and with gelatin coating and with and without crosslinking.

Gelatin coating can greatly enhance the mechanical property of expanded PCL nanofiber scaffolds. FIG. 4 provides photographs and SEM images of gelatin-coated, expanded PCL nanofiber scaffolds without and with crosslinking. FIG. 4 also shows photographs of expanded PCL nanofiber scaffolds and gelatin-coated, expanded PCL nanofiber scaffolds without and with crosslinking before and after immersing in water. Expanded PCL nanofiber scaffolds shrink after immersing in water. In contrast, gelatin-coated PCL nanofiber scaffolds can maintain their integrity after immersing in water. Notably, gelatin-coated (0.5%), expanded PCL nanofiber scaffolds after crosslinking absorbed water about 58 times of their weight, which is approximately one third higher than gelatin sponges. FIG. 4A provides images of expanded PCL nanofiber scaffolds coated with gelatin and without crosslinking. FIG. 4B provides a graph showing the increased weights of PCL nanofiber scaffolds after coating with gelatin. FIG. 4C provides a graph of the water absorption of expanded PCL nanofiber scaffolds without and with gelatin coating and without crosslinking. FIG. 4D provides images of expanded PCL nanofiber scaffolds coated with gelatin and with crosslinking. FIG. 4E provides a graph of the water absorption of expanded PCL nanofiber scaffolds without and with gelatin coating and with crosslinking. FIG. 4F provides SEM images of expanded PCL nanofiber scaffolds after gelatin coating without and with crosslinking.

Gelatin-coated (0.5%), expanded PCL nanofiber scaffolds was then compared with two commercial products (gelatin Gelfoam® (Ethicon, Somerville, NJ)) and gauze (see FIG. 5). Gelatin-coated (0.5%), expanded PCL nanofiber scaffolds demonstrated the highest water absorption capability. In addition, gelatin-coated (0.5%), expanded PCL nanofiber scaffolds showed the highest water uptake rate compared to gelatin Gelfoam® (Ethicon) and gauze. Gelatin-coated (0.5%), expanded PCL nanofiber scaffolds also showed better and faster shape recovery after squeezing. FIG. 5A provides images of expanded PCL nanofiber scaffolds coated with 0.5% gelatin, gauze, and gelatin surgical foam before and after immersing in water. FIG. 5B provides a graph of the water absorption of expanded PCL nanofiber scaffolds coated with 0.5% gelatin, gauze, and gelatin surgical foam. FIG. 5C provides images of expanded PCL nanofiber scaffolds coated with 0.5% gelatin, gauze, and gelatin surgical foam in water. FIG. 5D provides a graph of the water uptake rate for expanded PCL nanofiber scaffolds coated with 0.5% gelatin, gauze, and gelatin surgical foam. FIG. 5E provides images of the shape recovery of expanded PCL nanofiber scaffolds coated with 0.5% gelatin and gelatin surgical foam after squeezing. FIG. 5F provides a graph of the length recovery of expanded PCL nanofiber scaffolds coated with 0.5% gelatin and gelatin surgical foam.

Figure 6A:
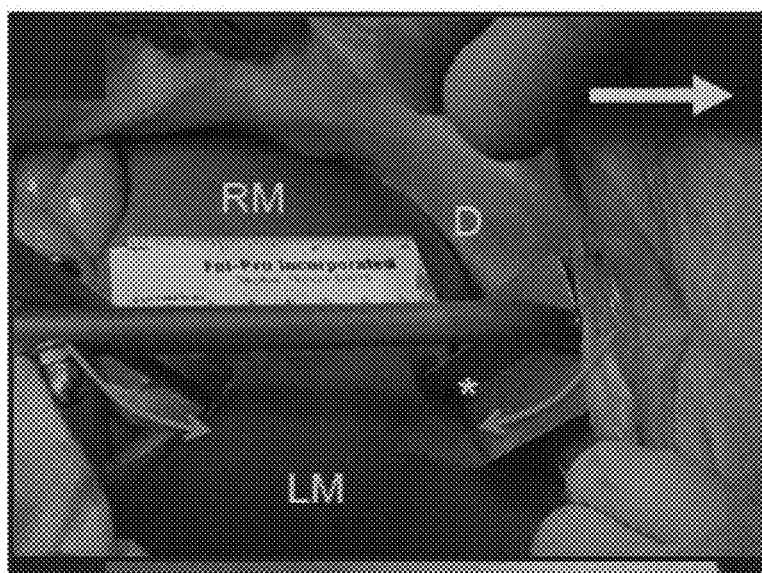
FIG. 6A provides a photograph of a stellate injury set-up to the liver. Liver injury clamp positioned with flat base on underside of liver. X-tines (asterisk) positioned over dome of liver, directly anterior to inferior vena cava (IVC). Curved arrows indicate rough trajectory of liver injury clamp. Two adjacent strikes were made with the clamp. Large arrow=cephalad. RM=right medial lobe of liver. LM=left medial lobe. D=diaphragm.
Figure 6B:
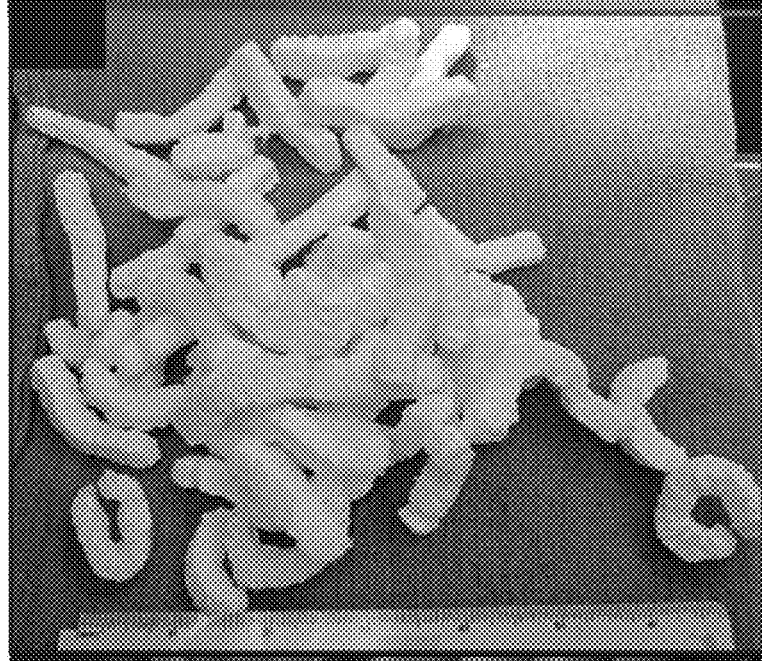
FIG. 6B provides a picture of gelatin-coated (0.5%), expanded PCL nanofiber scaffolds prior to use.
Figure 6C:
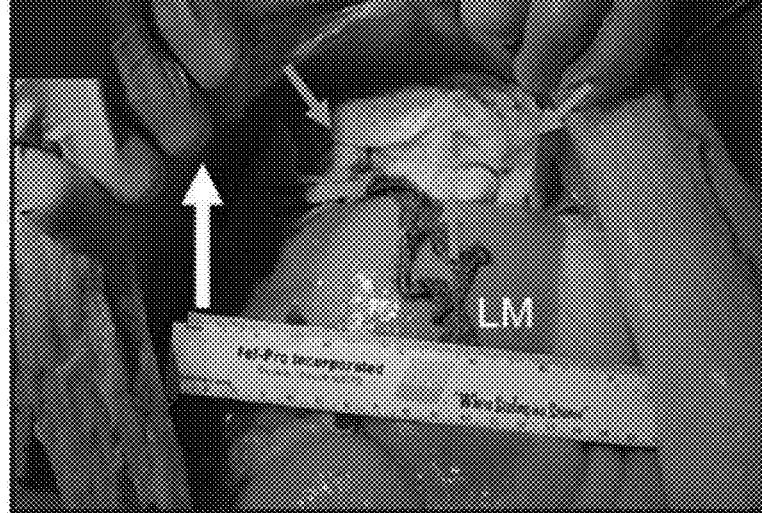
FIG. 6C provides a photograph of the upper abdomen/injury site (smaller arrows) after 1 hour of observation. Site was packed with cotton lap pads after placement of PCL nanofiber scaffolds. Minimal free blood was present and no active bleeding was observed at 1 hour. Large white arrow=cephalad.
Figure 6D:
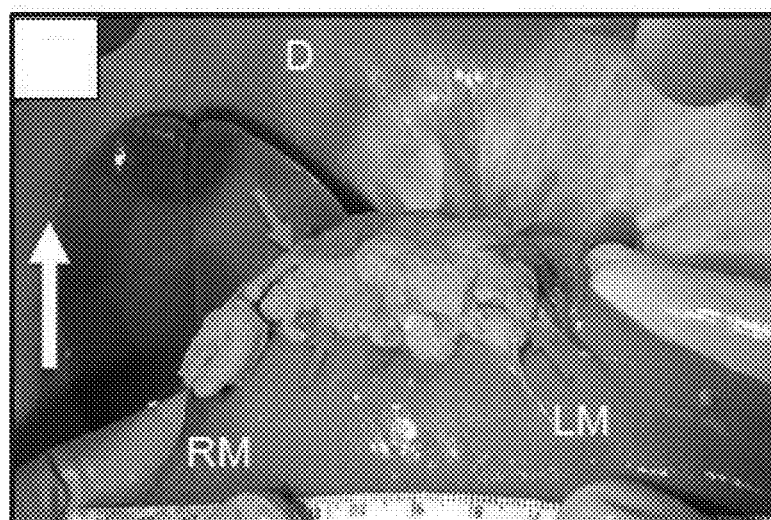
FIG. 6D provides a photograph of the injury site in situ after 1 hour observation period. Cotton lap pads were removed to show the PCL nanofiber scaffolds packed into the injury defect (smaller arrows). Large white arrow=cephalad.
Figure 6E:
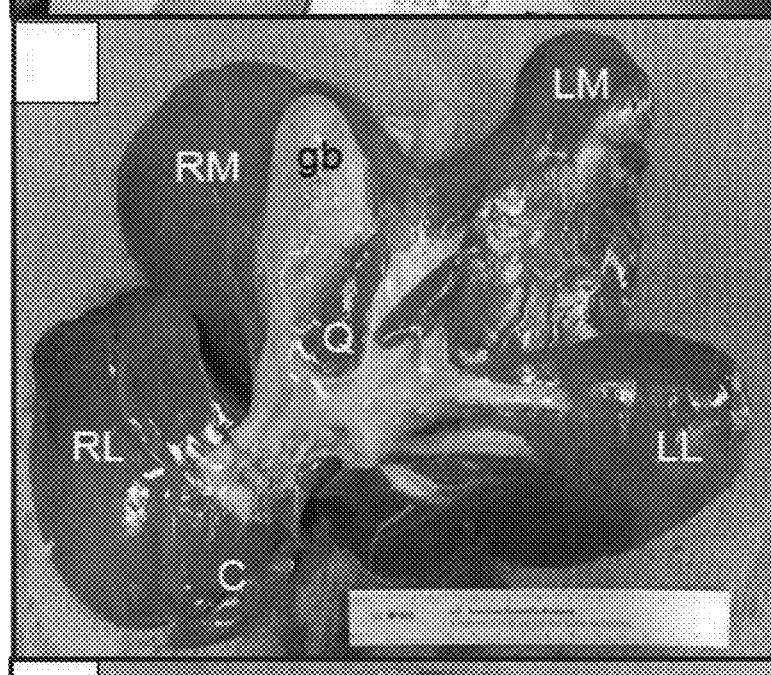
FIG. 6E provides a photograph of the inferior surface of the liver ex vivo. RL=right lateral lobe. LL=left lateral lobe. C=caudate lobe. Q=quadrate lobe. gb=gallbladder. Injury site is not visible.
Figure 6F:
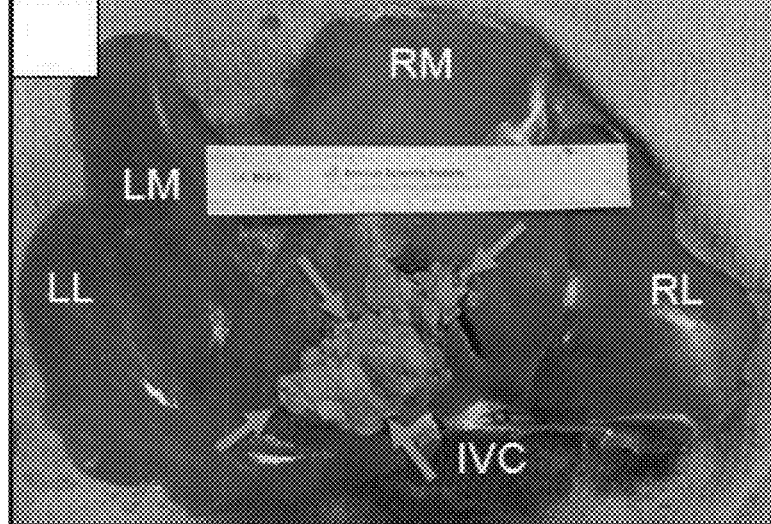
FIG. 6F provides a photograph of the superior surface of the liver ex vivo. Injury site visible with PCL nanofiber scaffolds packed into the defect (arrows), undisturbed from in situ condition.
Figure 7A:
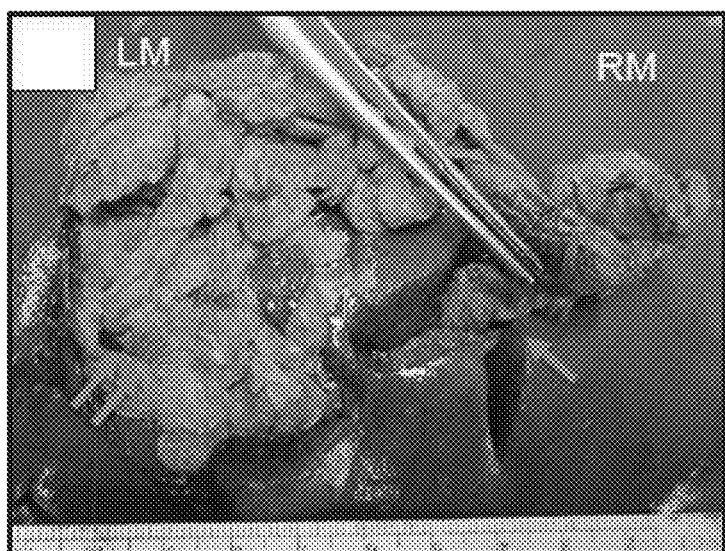
FIG. 7A provides a close-up photograph of the injury site with PCL nanofiber scaffolds being extracted from the injury site. Single arrow=site of right-sided clamp strike. Double arrow=site of left-sided clamp strike. Anterior is at top of image.
Figure 7B:
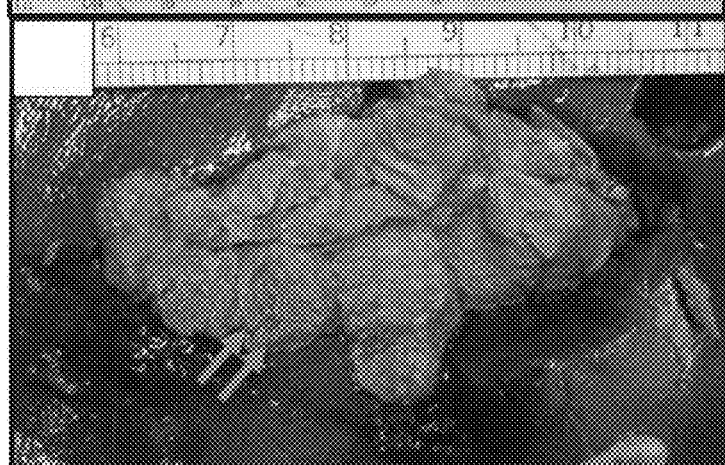
FIG. 7B provides a close-up photograph of the left-sided clamp strike. Anterior is at top of image.
Figure 7C:
FIG. 7C provides a photograph of PCL nanofiber scaffolds after extraction from liver wound.
Figure 8A:
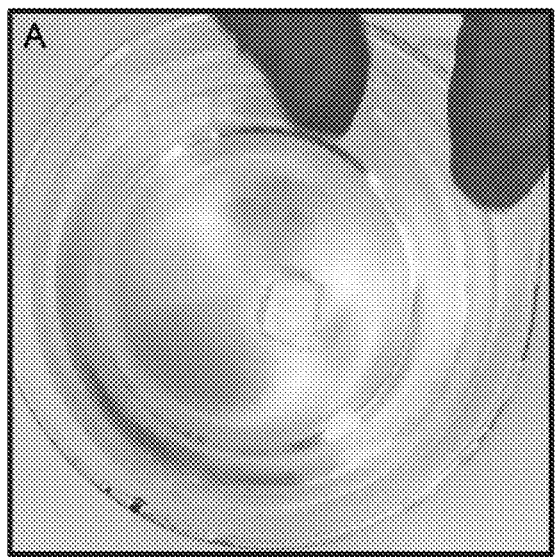
FIGS. 8A-8D provide photographs of intertwined disks placed in water for different times: 0 seconds (FIG. 8A), 1 second (FIG. 8B), 3 seconds (FIG. 8C), and 5 seconds (FIG. 8D).
Figure 8B:
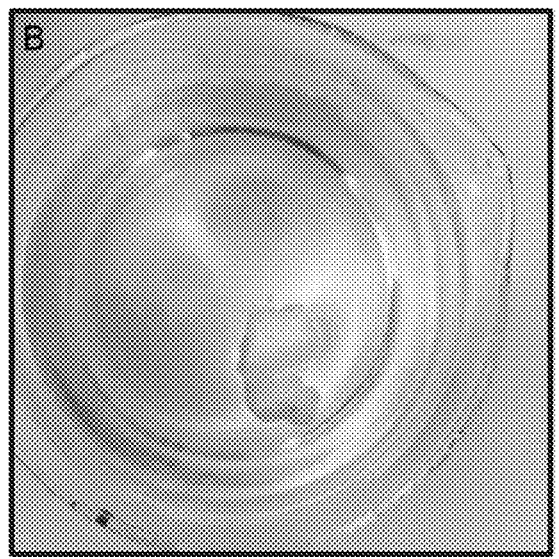
Figure 8C:
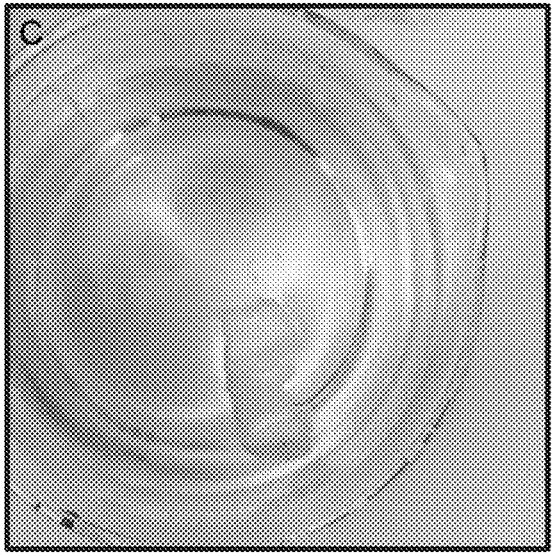
Figure 8D:
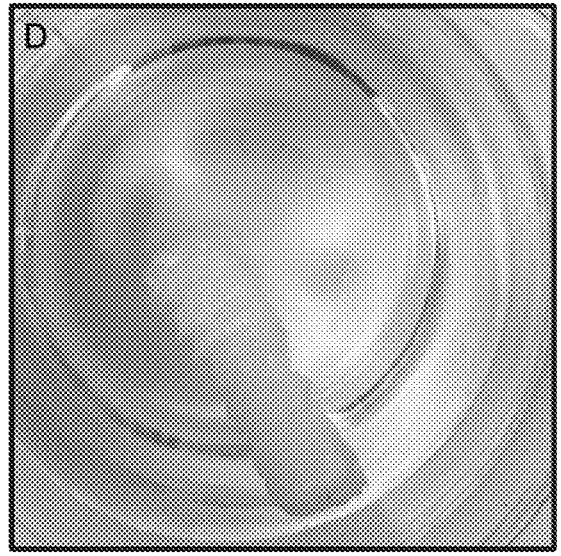

The gelatin-coated (0.5%), expanded PCL nanofiber scaffolds were further tested in vivo for hemostasis (FIGS. 6 and 7). Briefly, a stellate injury to the liver dome was performed as described hereinabove. Upon abdominal/chest exploration, the abdomen not distended or soft. Upon re-opening abdomen, minimal amount of blood was seen and there was no active hemorrhage from resection site (FIG. 6). The matrices and the overlying laparotomy pads were intact and in place. Subject easily survived 60 minutes with mean arterial pressure (MAP) in the 90's. The nanofiber scaffolds were in place at the injury site and were reasonably adherent to the wound (FIG. 7). Blood soaked through the matrices fully (FIG. 7).

The total blood loss (injury plus post-injury blood loss) was 1140 mL without treatment (Yanala et al., PLOS ONE (2014) 9(9):e108293). When the wound was treated with expanded PCL nanofiber scaffolds, the total blood loss was only 347 mL. Thus, the use of the expanded, PCL nanofiber scaffolds resulted in excellent hemostasis and reduction of blood loss.

FIG. 6A provides a photograph of a stellate injury set-up to the liver. Liver injury clamp positioned with flat base on underside of liver. X-tines (asterisk) positioned over dome of liver, directly anterior to inferior vena cava (IVC). Curved arrows indicate rough trajectory of liver injury clamp. Two adjacent strikes were made with the clamp. Large arrow=cephalad. RM=right medial lobe of liver. LM=left medial lobe. D=diaphragm. FIG. 6B provides a picture of gelatin-coated (0.5%), expanded PCL nanofiber scaffolds prior to use. FIG. 6C provides a photograph of the upper abdomen/injury site (smaller arrows) after 1 hour of observation. Site was packed with cotton lap pads after placement of PCL nanofiber scaffolds. Minimal free blood was present and no active bleeding was observed at 1 hour. Large white arrow=cephalad. FIG. 6D provides a photograph of the injury site in situ after 1 hour observation period. Cotton lap pads were removed to show the PCL PCL nanofiber scaffolds packed into the injury defect (smaller arrows). Large white arrow=cephalad. FIG. 6E provides a photograph of the inferior surface of the liver ex vivo. RL=right lateral lobe. LL=left lateral lobe. C=caudate lobe. Q=quadrate lobe. gb=gallbladder. Injury site is not visible. FIG. 6F provides a photograph of the superior surface of the liver ex vivo. Injury site visible with PCL nanofiber scaffolds packed into the defect (arrows), undisturbed from in situ condition.

Lastly, the expanded PCL nanofiber structures can be compressed into thin disks and packed with hydrophilic nanofiber bundles (for example PVP nanofiber bundles). The nanofiber bundles/yarns can be fabricated through different ways. One is to fabricate nanofiber membranes (e.g., of hydrophilic polymers (see examples above) such as PVP or PEO) and then cut the membranes into fine strips. The fine strips are twisted into nanofiber yarns/bundles. The nanofiber bundles can also be produced by a continuous way using a funnel or drawing from solutions. Such compressed disks can expand and recover their shapes very quickly after immersion in water (FIG. 8). These disks may be used as non-compressive hemostatic materials.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A nanofibrous structure comprising:
    a) an expanded, nanofiber structure comprising a plurality of nanofibers; and
    b) a coating comprising a material with water absorbing properties.

2. The nanofibrous structure of claim 1, wherein the nanofiber structure of a) is expanded by exposing a nanofiber structure to gas bubbles.

3. The nanofibrous structure of claim 2, wherein said gas bubbles are generated as a product of a chemical reaction.

4. The nanofibrous structure of claim 3, wherein said chemical reaction is the hydrolysis of sodium borohydride.

5. The nanofibrous of claim 3, wherein said exposure comprises immersing said nanofiber structure in a liquid comprising the reagents for said chemical reaction.

6. The nanofibrous structure of claim 1, wherein said nanofiber structure of a) comprises a plurality of uniaxially-aligned nanofibers, random nanofibers, and/or entangled nanofibers.

7. The nanofibrous structure of claim 1, wherein said nanofiber structure of a) comprises electrospun fibers.

8. The nanofibrous structure of claim 1, wherein said nanofibers comprise hydrophobic polymers.

9. The nanofibrous structure of claim 8, wherein said hydrophobic polymer is poly(caprolactone).

10. The nanofibrous structure of claim 1, wherein said coating comprises a hydrogel.

11. The nanofibrous structure of claim 1, wherein said coating comprises a material selected from the group consisting of gelatin, chitosan, starch, pectin, cellulose, methylcellulose, sodium polyacrylate, and starch-acrylonitrile co-polymers.

12. The nanofibrous structure of claim 11, wherein said coating comprises gelatin.

13. The nanofibrous structure of claim 1, wherein said coating is crosslinked.

14. The nanofibrous structure of claim 1, further comprising a therapeutic agent.

15. The nanofibrous structure of claim 14, wherein said therapeutic agent is a blood coagulation agent, an antimicrobial, or a growth factor.

16. The nanofibrous structure of claim 1, wherein the nanofiber structure of a) is expanded by exposing a nanofiber structure to gas bubbles, wherein said nanofiber structure of a) comprises electrospun fibers, and wherein said coating comprises a hydrogel.

17. The nanofibrous structure of claim 16, wherein said hydrogel is crosslinked.

18. A method for the inhibiting, preventing, and/or treating bleeding and/or hemorrhaging in a subject in need thereof, said method comprising administering the nanofibrous structure of claim 1 to the site of bleeding.

19. A method of synthesizing the nanofibrous structure of claim 1.

20. A microfibrous structure comprising:
   a) an expanded, microfiber structure comprising a plurality of microfibers; and
   b) a coating comprising a material with water absorbing properties.

21. The microfibrous structure of claim 20, wherein the microfiber structure of a) is expanded by exposing a microfiber structure to gas bubbles.

22. The microfibrous structure of claim 21, wherein said gas bubbles are generated as a product of a chemical reaction.

23. The microfibrous structure of claim 22, wherein said chemical reaction is the hydrolysis of sodium borohydride.

24. The microfibrous of claim 22, wherein said exposure comprises immersing said microfiber structure in a liquid comprising the reagents for said chemical reaction.

25. The microfibrous structure of claim 20, wherein said microfiber structure of a) comprises a plurality of uniaxially-aligned microfibers, random microfibers, and/or entangled microfibers.

26. The microfibrous structure of claim 20, wherein said microfiber structure of a) comprises electrospun fibers.

27. The microfibrous structure of claim 20, wherein said microfibers comprise hydrophobic polymers.

28. The microfibrous structure of claim 27, wherein said hydrophobic polymer is poly(caprolactone).

29. The microfibrous structure of claim 20, wherein said coating comprises a hydrogel.

30. The microfibrous structure of claim 20, wherein said coating comprises a material selected from the group consisting of gelatin, chitosan, starch, pectin, cellulose, methylcellulose, sodium polyacrylate, and starch-acrylonitrile co-polymers.

31. The microfibrous structure of claim 30, wherein said coating comprises gelatin.

32. The microfibrous structure of claim 20, wherein said coating is crosslinked.

33. The microfibrous structure of claim 20, further comprising a therapeutic agent.

34. The microfibrous structure of claim 33, wherein said therapeutic agent is a blood coagulation agent, an antimicrobial, or a growth factor.

35. The microfibrous structure of claim 20, wherein the microfiber structure of a) is expanded by exposing a microfiber structure to gas bubbles, wherein said microfiber structure of a) comprises electrospun fibers, and wherein said coating comprises a hydrogel.

36. The microfibrous structure of claim 35, wherein said hydrogel is crosslinked.

37. A method for the inhibiting, preventing, and/or treating bleeding and/or hemorrhaging in a subject in need thereof, said method comprising administering the microfibrous structure of claim 20 to the site of bleeding.

38. A method of synthesizing the microfibrous structure of claim 20.

* * * * *